(12) United States Patent
Stewart et al.

(10) Patent No.: US 7,157,427 B2
(45) Date of Patent: Jan. 2, 2007

(54) ANTIMICROBIAL PROTEINS FROM THE SPO1 BACTERIOPHAGE

(75) Inventors: Charles R. Stewart, Houston, TX (US); A. Yousif Shamoo, Houston, TX (US)

(73) Assignee: Rice University, Houston, TX (US)

( * ) Notice: Subject to any disclaimer, the term of this patent is extended or adjusted under 35 U.S.C. 154(b) by 0 days.

(21) Appl. No.: 10/809,761

(22) Filed: Mar. 25, 2004

(65) Prior Publication Data

US 2005/0054571 A1 Mar. 10, 2005

Related U.S. Application Data

(60) Provisional application No. 60/457,287, filed on Mar. 25, 2003.

(51) Int. Cl.
*A61K 38/00* (2006.01)
*C07K 14/00* (2006.01)

(52) U.S. Cl. ........................ 514/12; 530/350

(58) Field of Classification Search ............... 435/5; 530/350

See application file for complete search history.

(56) References Cited

U.S. PATENT DOCUMENTS

2001/0026795 A1 10/2001 Merril et al.
2001/0043924 A1 11/2001 Carlton et al.

OTHER PUBLICATIONS

Sampath et al., "Roles of Specific Genes in Host-Takeover of *B. subtilis* by Bacteriophage", Abstracts of the General Meeting of the American Society for Microbiology. 2002. v.102, p. 302.*
Wie. Ph.D. Thesis: A host-shutoff early gene of *Bacillus subtilis* bacteriophage SPO1. Rice University. 1994.*
Sampath et al., "Roles of Specific Genes in Host-Takeover of *B. subtilis* by Bacteriophage", Abstracts of the General Meeting of the American Society for Microbiology. 2002. v.102, p. 302.*
Weiss et al. In Vivo Activity of Peptidic Prodrugs of Novel Aminomethyl Tetrahydrofuranyl-1 beta-Methylcarbapenems. Antimicrobial Agents and Chemotherapy. 1999. vol. 43, No. 3, pp. 460-464.*
Air E.L., et al.(2002) Nature Med. 8:179-183.
Andrade-Gordon P. et al. (1999) Proc. Natl. Acad. Sci. U.S. 96:12257-12262.
Dedonder, R.A., et al. (1977) Appl. Environ. Mirobiol. 33: 989-993.
Fotsch, C., et al. (2003) Bioorganic & Medicinal Chemistry Letters 13: 2337-40.
Gadek, T.R., et al. (2002) Science 295: 1086-9.
Greene, J.R., et al. (1982) J. Virol. 41: 715-20.
Greene, J.R., et al. (1984) Proc. Natl. Acad. Sci. USA 81: 7031-5.
Hendrickson W.A., et al. (1997) In Methods in Enzymology. 276: 494-522.
Pedulla M.L., et al. (2003) Corrected Sequence of the Bacteriophage P22 Genome. 185: 1475-77.
Ireton, K., et al. (1993) Genes & Dev. 7: 283-94.
Kim, L., et al. (1996) Gene 181: 71-6.
Kobayashi, K., et al. (2003) Proc. Natl. Acad. Sci. USA 100: 4678-83.
Legrain, P. (2002) Nature Biotechnology 20: 128-9.
Malys, N., et al. (2002) J. Mol. Biol. 319: 289-04.
Martin L., et al. (2003) Nature Biotech. 21:71-76.
Miyazaki K., et al. (2000) J. Mol. Biol. 297:1015-1026.
Noirot-Gros, M.F., et al. (2002) Proc. Natl. Acad. Sci. U.S.A. 99: 8342-8347.
Ohkanda, J., et al. (2001) Bioorganic & Medicinal Chemistry Letters 11: 761-764.
Okubo, S., et al. (1972) Biken J. 15: 81-97.
Salvemini D., et al. (1999) Science 286:304-306.
Salvemini, D., et al. (2002) Nature Reviews 1: 367-74.
Sayers, J.R. (1996) Meth. Enz. 275: 227-38.
Scarlato, V., and S. Gargano (1992) Gene 118: 109-113.
Scott, J.K. (2001) in "Phage Display" C.F. Barbas, et al. (eds.) Cold Spring Harbor Laboratory Press, Cold Spring Harbor, New York, pp. 4.1-4.13.
Shamoo, Y., (1995) Nature 376: 362-6.
Shamoo Y., et. al. (1997) Nat. Struc. Biol. 4:215-222.
Shamoo, Y., and T.A. Steitz. (1999) Cell 99: 155-166.
Barrett, J.F. et al., Antibacterial agents that inhibit two-component signal transduction systems, Proc. Natl. Acad. Sci. USA, Apr. 1998, pp. 5317-5322, vol. 95.
Biswas, B. et al., Bacteriophage Therapy Rescues Mice Bacteremic from a Clinical Isolate of Vancomycin-Resistant Enterococcus Faecium, Infection and Immunity, Jan. 2002, pp. 204-210, vol. 70(1).
Breithaupt, H., The new antibiotics—Can novel antibacterial treatments combat the rising tide of drug-resistant infections?, Nature Biotechnology, Dec. 1999, pp. 1165-1169, vol. 17.
Drews, J., Drug Discovery: A Historical Perspective, Science, Mar. 2000, pp. 1960-1964, vol. 287.
Dixon, B., Genomics and Innovation in Antibiotics, ASM News, 2002, pp. 106-107, vol. 68.
Einarson, M. et al., Identification of Protein-Protein Interactions with Glutathione-S-Transferase Fusion Proteins, Cold Spring Harbor Laboratory Press, 2001, pp. 37, 57.
Erdmann, J., Bacteria Resistant to Drugs Draw Scrutiny of Biofirms, Genetic Engineering News, May 1999, pp. 1, 19, 50, 58; vol. 19(10).
Glaser, V., Rational Drug Design Plays Big Part in Drug Discovery, Genetic Engineering News, Nov. 1, 1998, pp. 1, 8.
Golemis, E., Protein-Protein Interactions—A Molecular Cloning Manual, Cold Spring Harbor Laboratory Press, 2002, 2 pp.
Harwood, C. et al., Molecular Biological Methods for Bacillus, 1990, 2 pp., John Wiley & Sons Ltd, West Sussex, England.
Johnson, C. et al., Novel antimicrobial targets from combined pahtogen and host genetics, PNAS, Feb. 2000, pp. 958-959, vol. 97(3).

(Continued)

*Primary Examiner*—Karen Cochrane Carlson
*Assistant Examiner*—Suzanne M. Noakes

(57) ABSTRACT

Anti-bacterial peptides are provided which are derived from the bacteriophage SPO1.

11 Claims, 12 Drawing Sheets

OTHER PUBLICATIONS

Miller, J., A Short Course in Bacterial Genetics, Cold Spring Harbor Laboratory Press, 1992, 2 pp.

Persidis, A., Antibacterial and antifungal drug discovery, Nature Biotechnology, Nov. 1999, pp. 1141-1142, vol. 17.

Sampath, A. et al., Genetic Analysis of Host-takeover in SPO1 infection of *B. subtilis*, Abstracts of the Fourteenth Evergreen International Phage Biology Meeting, Aug. 2001, Poster Section, p. 9.

Sampath, A. et al., Role of SPO1 Genes 44, 50, and 51 in Host-takeover and Bacterial Cell Death, Abstracts of the Fourteenth Evergreen International Phage Biology Meeting, Aug. 2001, p. 5.

Shamoo, Y. et al., Crystal structure of the two RNA binding domains of human hnRNP A1 at 1.75 A resolution, Nature Structural Biology, Mar. 1997, pp. 215-222, vol. 4(3).

Zhang, H. et al., New Perspectives on Anti-HER2/Neu Therapeutics, Drug News Perspect, pp. 325-329, vol. 13(6), Aug. 2000.

Spee J.H., et al. (1993) Nucleic Acids Res. 21:777-778.

Smith, R.A., et al. (2001) Bioorganic and Medical Chemistry Letters 11: 2951-4.

Stewart, C.R. (1993) in *Bacillus subtilis* and other gram-positive bacteria (A. Sonenshein, J.A. Hoch, and R. Losick, eds. American Society for Microbiology) pp. 813-829.

Stewart C.R., et al.(1998) Virology 246:329-340.

Stewart C.R. (1999) SPO1 Phage (Myoviridae), in Encyclopedia of Virology (2nd Edition, Webster, R.G., and Granoff, A., eds.) pp. 1681-1685.

Stewart, C.R. et al. (Aug. 8-13, 2001) In Abstracts of the Fourteenth Evergreen International Phage Biology Meeting.

Tatusova, T.A. & T.L. Madden (1999) FEMS Microbiol. Lett. 174: 247-50.

Tian S.S., et al. (1998) Science 281:257-259.

Vandeyar, M.A., and S. A. Zahler (1986) J. Bacteriol. 167: 530-4.

Wanner, B.L. (1986) J. Mol. Biol. 191: 39-58.

Wei P. & Stewart C.R. (1993) A cytotoxic early gene of *Bacillus subtilis* bacteriophage SPO1. J Bacteriol. 175(24):7887-900.

Wei P. & Stewart C.R. (1995) Genes that protect against the host-killing activity of the E3 protein of *Bacillus subtilis* bacteriophage SPO1, J. Bacteriol. 177, 2933-2937.

Willats, W.G.T. (2002) Plant Molecular Biology 50: 837-54.

Wrighton, N., and D. Gearing (1999) Nature Biotech. 17: 1157-8.

Duckworth, D. et all, "Bacteriophages: potential treatment for bacterial infections", BioDrugs 2002;16(1):57-62.

Cudic, M. et al., "Intracellular targets of antibacterial peptides", Curr Drug Targets Apr. 2002;3(2):101-6.

Sadler, K. et al., "Translocating proline-rich peptides from the antimicrobial peptide bactenecin 7", Biochemistry Dec. 3, 2002;41(48):14150-7.

Kutter E., "Phage Therapy: Bacteriophages as Antiobiotics" http://www.evergreen.edu/phage/phagetherapy.html, p. 1-24, Nov. 1997.

* cited by examiner

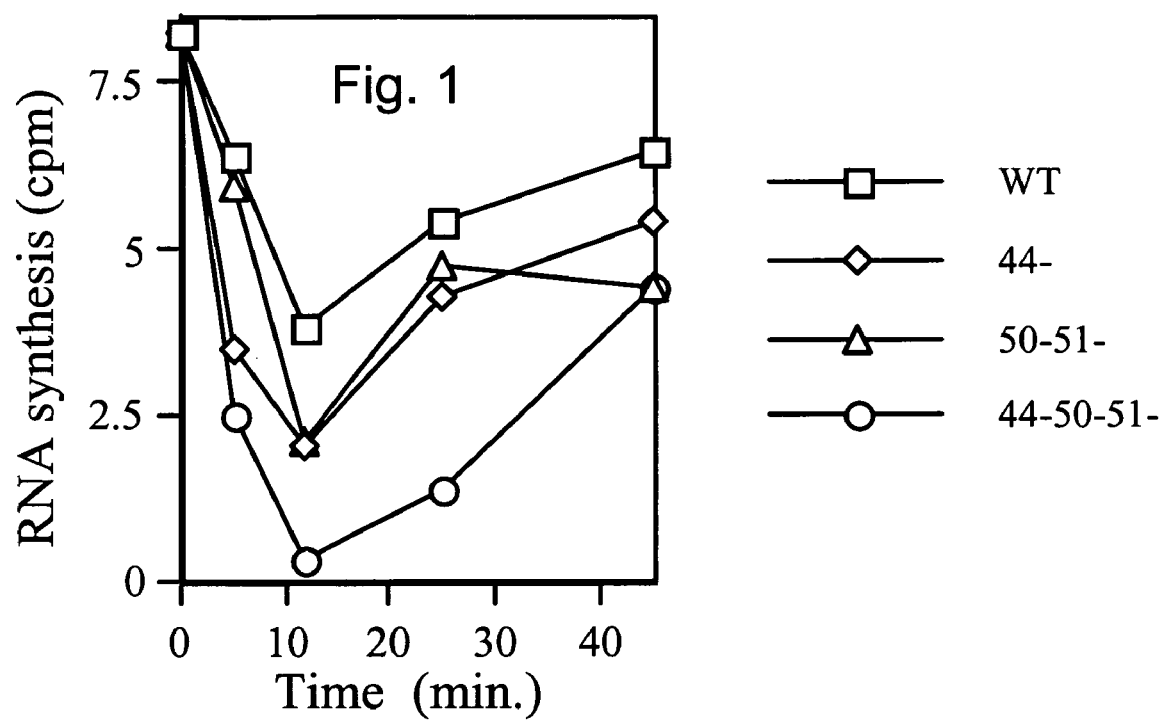

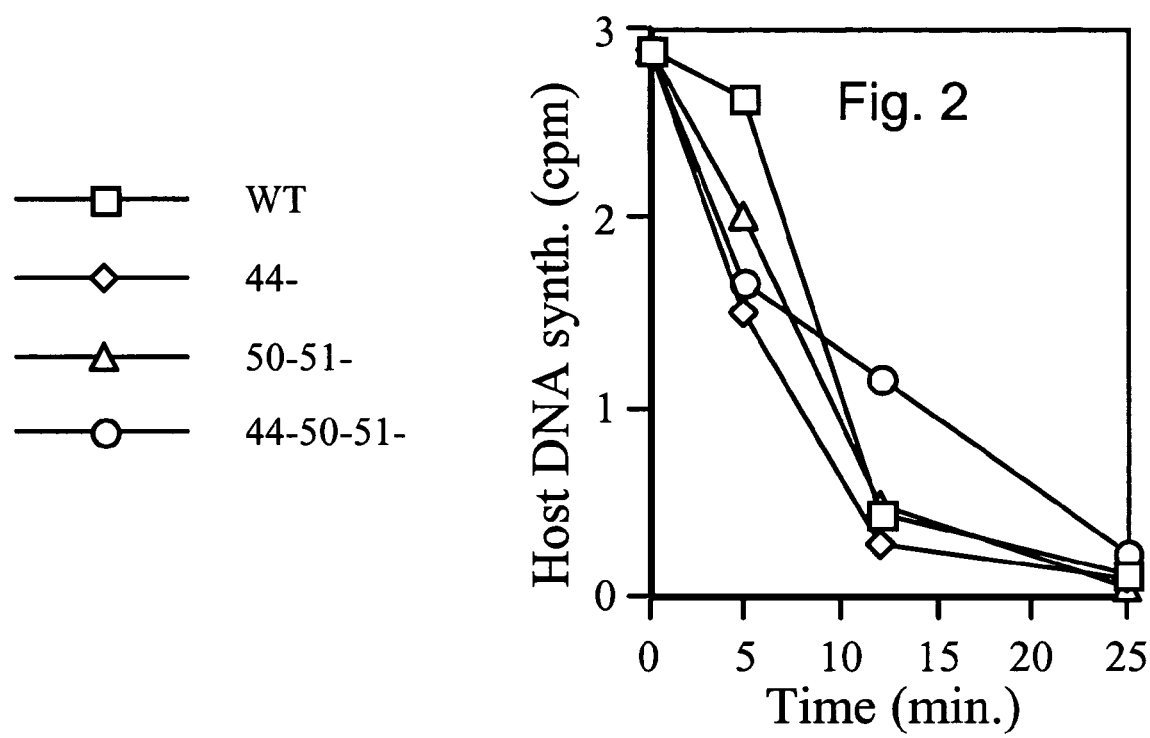

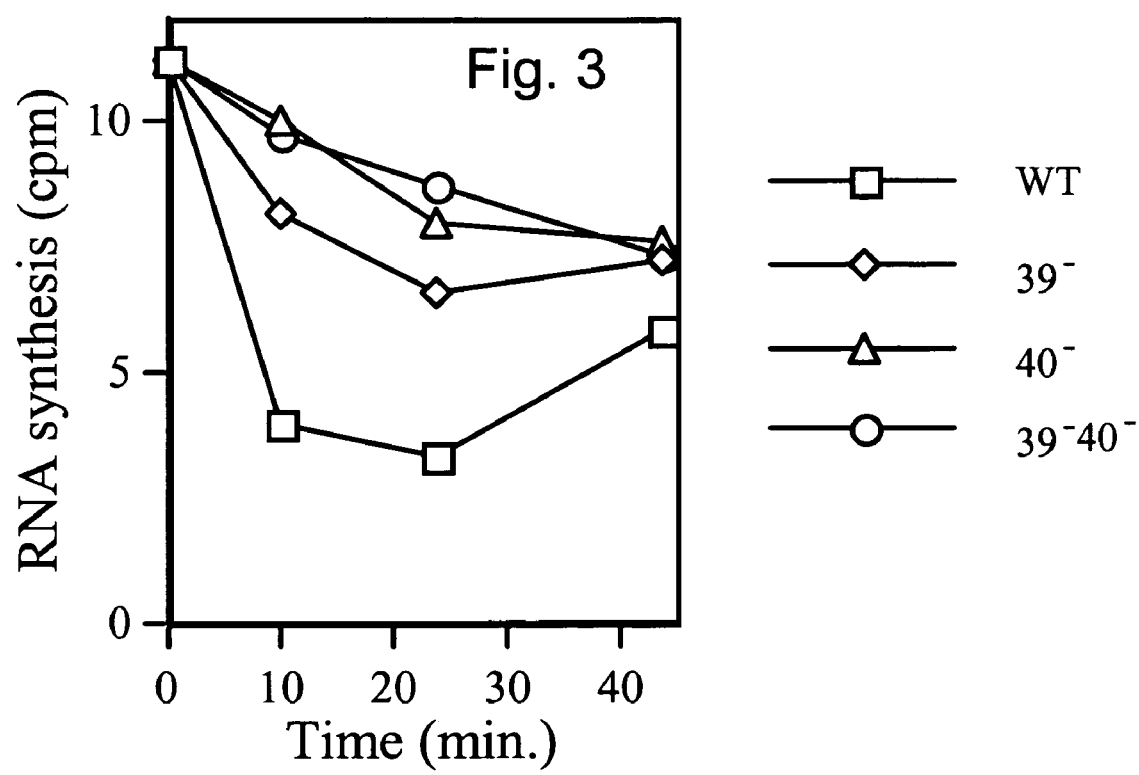

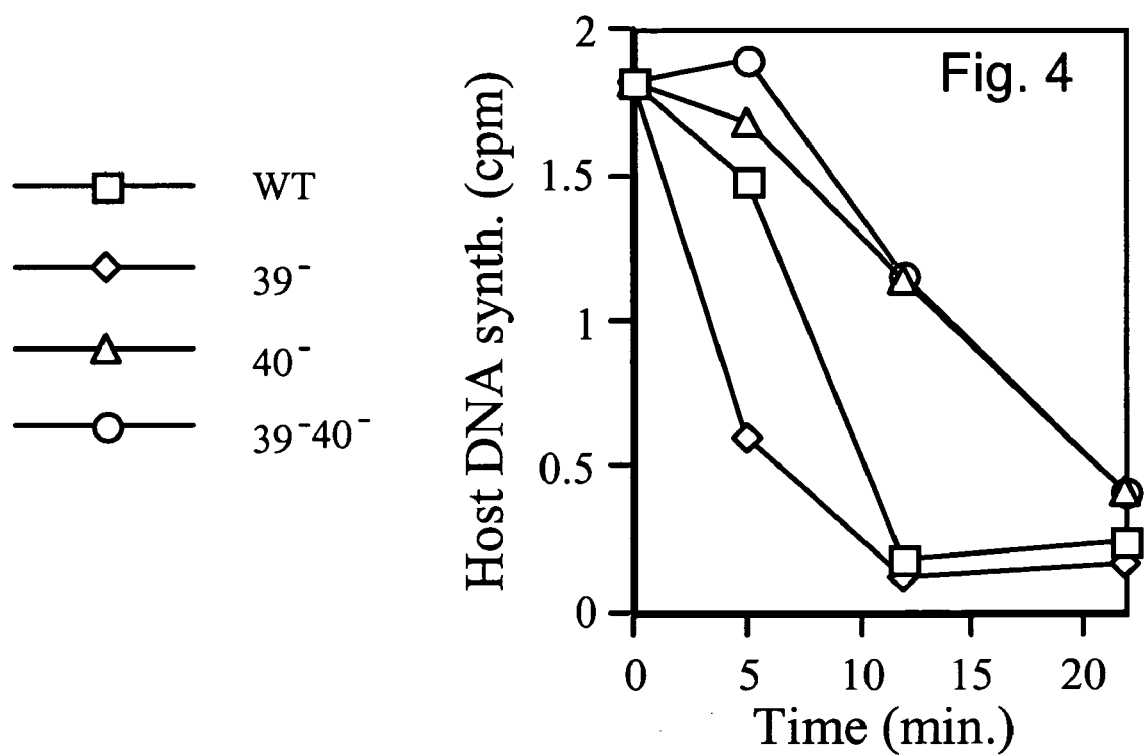

FIG. 5. Gene-Specific Expression Patterns.
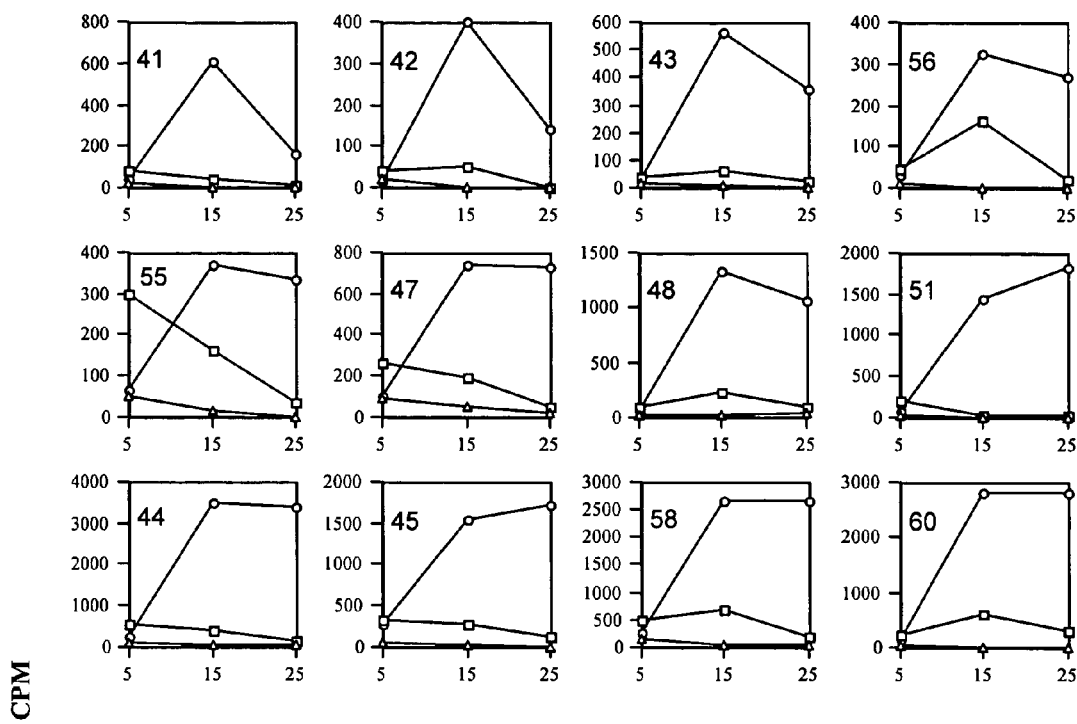
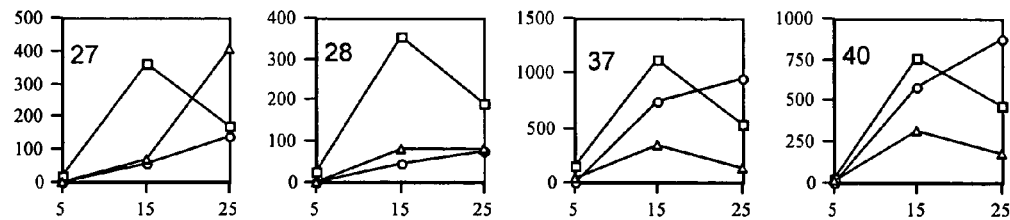
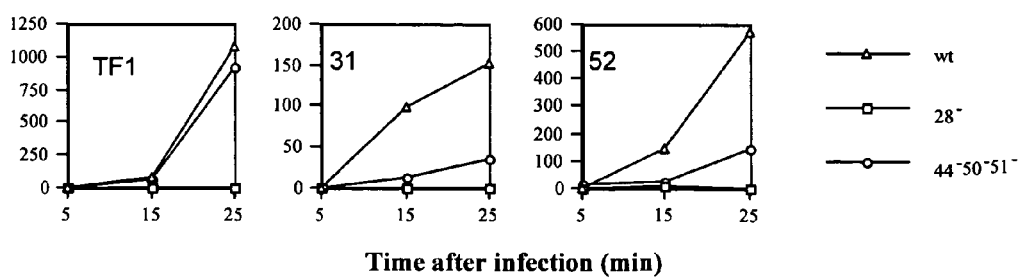

FIG. 6. Differential Effects of Mutations on Immediate-Early, Delayed-Early, and Middle Transcription.
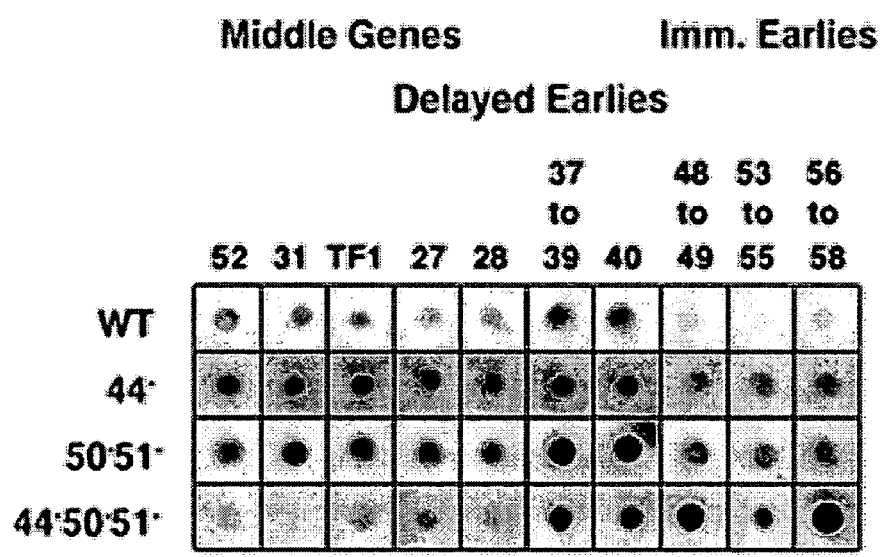

FIG. 7 (A and B). Distinguishable Effects of Genes 50 and 51.
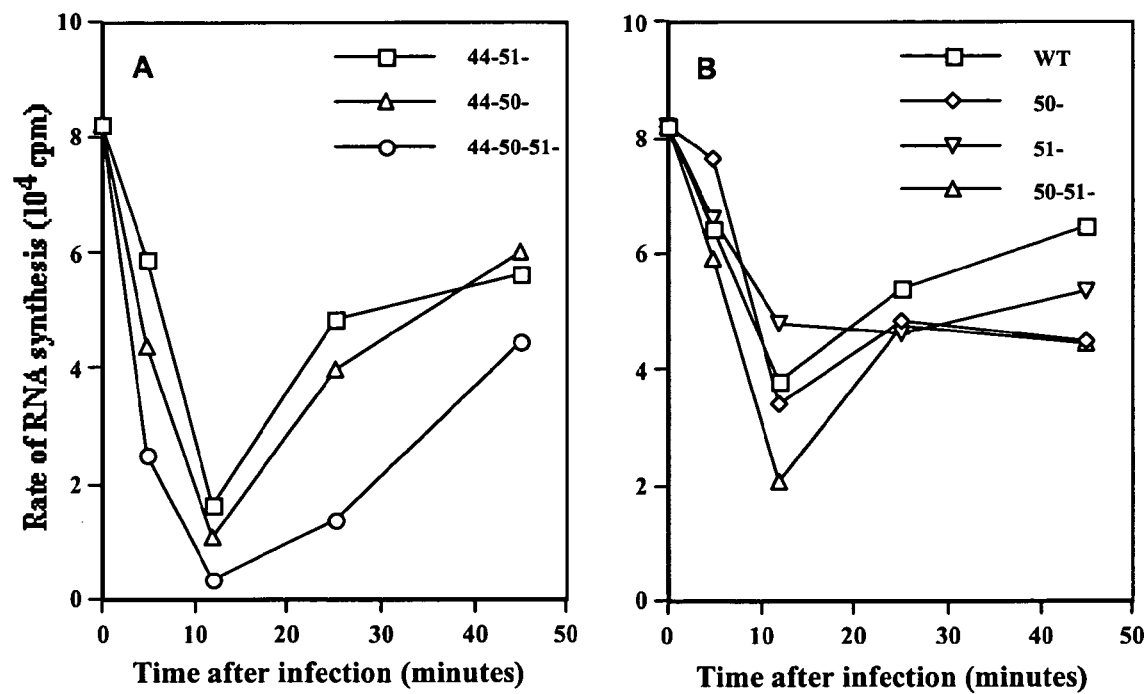

FIG. 8. Expression of SPO1 GP44 in *E. coli*.
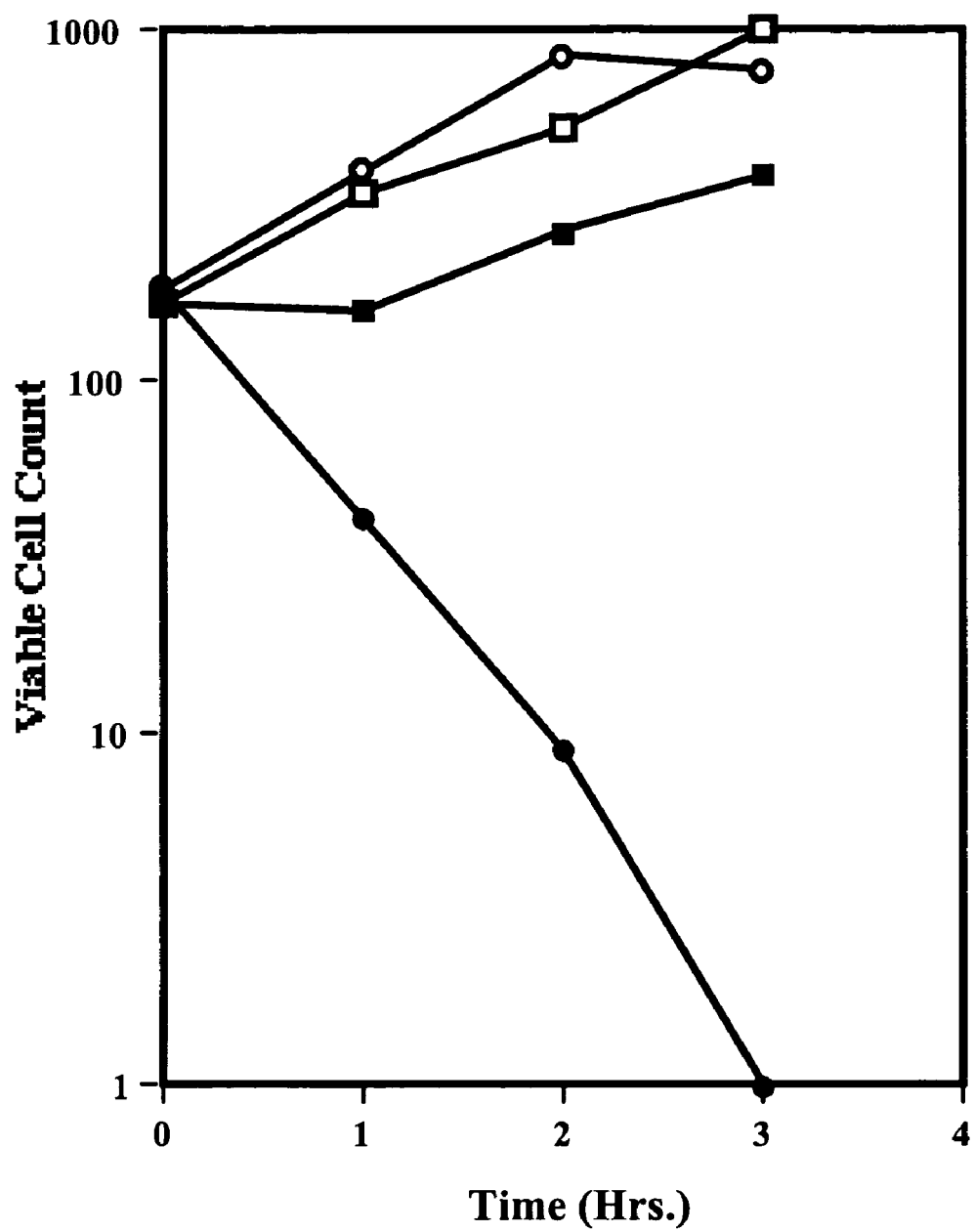

FIG 9. Effect of Gene 40, Gene 44, Gene 50 and Gene 51 on Phage DNA Synthesis.
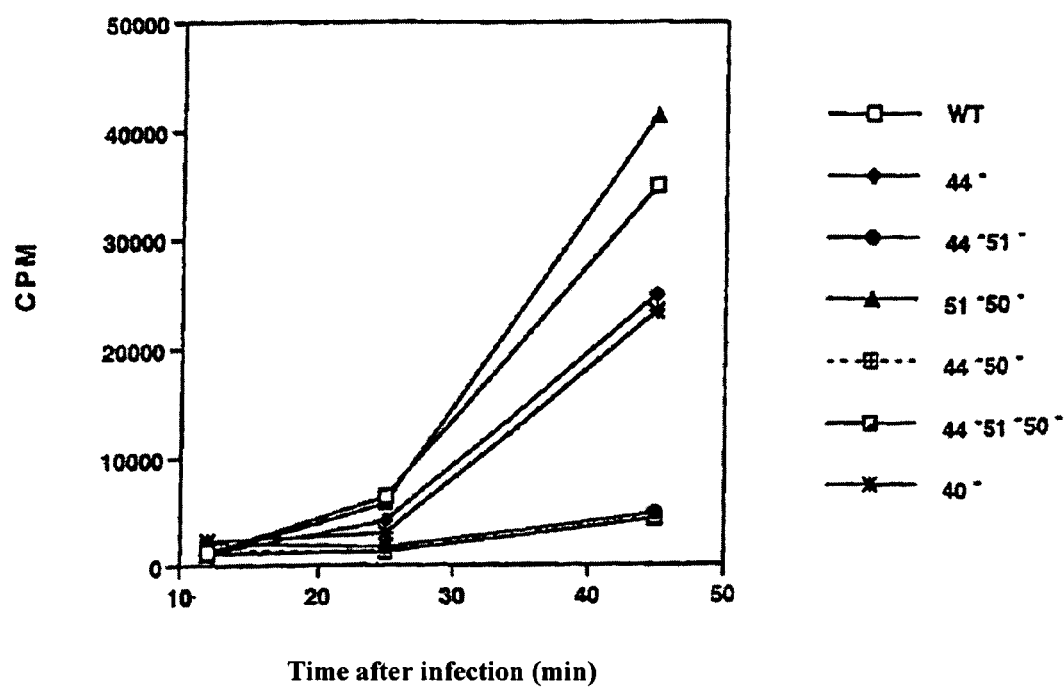

FIG 10. Effect of Gene 44, Gene 50 and Gene 51 on Single Step Growth Curves.
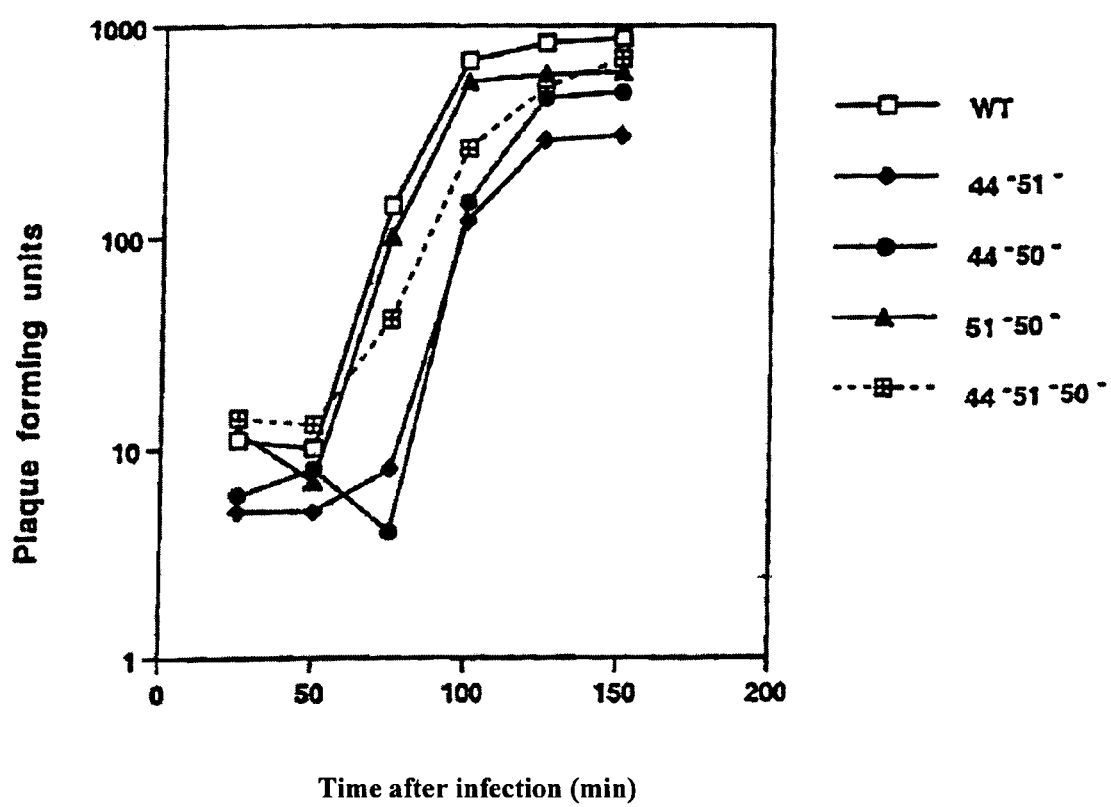

SEQUENCE LISTING

<160> NUMBER OF SEQ ID NOS: 24

<210> SEQ ID NO 1
<211> LENGTH: 31
<212> TYPE: PRT
<213> ORGANISM: SPO1 Bacteriophage

<400> SEQUENCE: 1

Met Ser Asp Val Ile Ile Pro Phe Leu Thr Ser Ala Val Thr Ala Phe
1               5                   10                  15

Ile Val Ala Tyr Leu Leu Asp Arg Trp Tyr Ile Lys Arg Arg Arg
            20                  25                  30

<210> SEQ ID NO 2
<211> LENGTH: 190
<212> TYPE: PRT
<213> ORGANISM: SPO1 Bacteriophage

<400> SEQUENCE: 2

Met Ser Val Gln Ile Lys His Gly Asn Lys Thr Phe Val Val Asp Pro
1               5                   10                  15

Ser Gly Asp Val Lys Glu Gly Ser Tyr Val Leu Tyr Leu Tyr Glu Tyr
            20                  25                  30

Arg Leu Gly Glu Val Asp Val Gly Arg Val Ser Glu Val Ala Asn Asp
        35                  40                  45

Gly Arg Leu Tyr Leu Asp Gly Pro Gly Val Ile Val Thr Leu Asp Gln
    50                  55                  60

Pro Phe Ile Leu Leu Lys Glu Val Val Glu Glu Glu Asp Glu Asp
65                  70                  75                  80

Asp Arg Ile Asp Ala Glu Phe His Asn Asp Pro Leu Leu Arg Lys Leu
                85                  90                  95

Glu Asn Thr Thr Glu Lys Leu Thr Pro Glu Glu Thr Gln Leu Ala Gln
            100                 105                 110

Trp Thr Thr Met Thr Arg Val Phe Ser His Asp Leu Lys Lys Gly Ile
        115                 120                 125

Pro Tyr Ala Ile Lys His Lys Asn Ser Gly Asn Ile Leu Tyr Gly Leu
    130                 135                 140

Tyr Ser Gly Leu Leu Asn Pro Val Thr Ala Leu Phe Arg His Leu Asn
145                 150                 155                 160

Glu Glu Ser Lys Ile Ser Ile Glu Gln Leu Lys Ser Gly Leu Ile Glu
                165                 170                 175

Ile Tyr Glu Val Val Glu Asp Glu Glu Glu Ser Ile Trp Asn
            180                 185                 190

<210> SEQ ID NO 3
<211> LENGTH: 255
<212> TYPE: PRT
<213> ORGANISM: SPO1 Bacteriophage

<400> SEQUENCE: 3

Met Glu Leu Asn Leu Asp Ile Tyr Val Asp Tyr Lys Asp Lys Arg Tyr
1               5                   10                  15

Lys Ala Glu Gly Tyr Tyr Gly Pro Ser Val Gly Asp Leu Val Leu Ile
            20                  25                  30

Phe Met Asp Met Glu Leu Glu Gly Ala Thr Val Gln Glu Val Ala Arg
        35                  40                  45

```
Ile Glu Gly Ser Glu Ile His Leu Arg Thr Pro Asn Gly Asn Glu Pro
 50                  55                  60

Ser Tyr Arg Tyr Met Gly Gln Tyr Leu Ile Leu Lys Pro Tyr Gly Ser
 65                  70                  75                  80

Ser Asp Pro Arg Gly Asp Ile Leu Val His Glu Asp Val Gln Tyr Val
                 85                  90                  95

Arg Val Asp Ala Gln Ala Met Pro Gly Asp Leu Ile Glu Ala Leu Glu
                100                 105                 110

Pro Asn Lys Leu Pro Phe Ser Gly Lys Arg Phe Lys Tyr Arg Pro Ala
                115                 120                 125

Val Leu Glu Val Glu Tyr Val Leu Thr Lys Asp Glu Gln Val Leu Gln
                130                 135                 140

Leu Glu Asn Gly Lys Ser Tyr Ser Gly Ala Tyr Arg Val Leu Ile Pro
145                 150                 155                 160

Arg Met Gly Val Leu Pro Pro Lys Thr His Ile Tyr Thr Thr His Lys
                165                 170                 175

His Val Phe Met Glu Asp Val Phe Val Leu Gly Asn Ser Tyr Glu Leu
                180                 185                 190

Ser Ser Pro Asn Asp Val Glu Met Thr Pro Ile His Ala Val Phe Thr
                195                 200                 205

Gly Phe Ser Lys Asn Arg Asp Glu Ala Ile Phe Val Asn Pro Tyr Tyr
210                 215                 220

Asn Asp Asp Gly Val Thr Gly Thr Met Ile Thr Val Ser Asp Leu Leu
225                 230                 235                 240

Thr Gly Lys Trp Asp Ile Thr Pro Leu Val Pro Lys Lys Gly Val
                245                 250                 255

<210> SEQ ID NO 4
<211> LENGTH: 350
<212> TYPE: PRT
<213> ORGANISM: SPO1 Bacteriophage

<400> SEQUENCE: 4

Met His Ile Tyr Thr Tyr Trp Gly Leu Lys Tyr Val Pro Ser Asn Ser
 1               5                  10                  15

Thr Met Val Ala Lys Glu Gly Asp Leu Ile Leu Leu Gly Asn Glu Val
                 20                  25                  30

His Lys Val Val Lys Val Leu His Arg Phe Arg Asn Ile Thr Asp Leu
                 35                  40                  45

Gln Ile Thr Asn Trp Lys Gly Thr Glu Thr Arg Tyr Asn Leu His Val
 50                  55                  60

Thr Glu Tyr Lys Val Leu Val Pro Tyr Asp Thr His Lys Glu Glu Asn
 65                  70                  75                  80

Glu Ala Met Ser Asp Ser Leu Ile Thr His Asn Gly Lys Asp Tyr Val
                 85                  90                  95

Leu Cys Lys Ile Pro Ala Arg Val Gly Asp Leu Ile Arg Thr Glu Asp
                100                 105                 110

Lys Arg Val Trp Glu Val Leu Gln Lys Ser Lys Asp Gly Leu Val Leu
                115                 120                 125

Tyr Asn Glu Glu Lys Gly Glu Gln Arg Ser Ala Val Tyr Ser Glu Ile
                130                 135                 140

Gly Pro Tyr His Val Leu Val Pro Arg Asp Thr Asp Thr His Thr Pro
145                 150                 155                 160

Thr Arg Glu Glu Leu Ala Ala Val Ile Met Asn Lys Ala Phe Thr Arg
                165                 170                 175
```

```
Thr Glu Thr Gln Asp Ser Gln Glu Asp Thr Gly Thr His Lys Gly Leu
            180                 185                 190

Gly Leu Thr Gly Thr Asp Leu Tyr His Ser Leu Arg Asp Leu Asp Ala
        195                 200                 205

Lys Val Gln Ser Gly Tyr Tyr Thr Ala Thr Glu Asn Glu Glu Asp Val
    210                 215                 220

Lys Ser Glu Ile Glu Ala Thr Lys Lys His Met Lys Ala Val Lys Glu
225                 230                 235                 240

Ser Gly Lys Thr Val Asn Asp Tyr Arg Lys Glu Glu Asn Thr Lys Arg
                245                 250                 255

Cys Lys Leu Lys Ala Leu Thr Asn Lys Phe Asn Arg Leu Phe Leu Lys
            260                 265                 270

Ser Val Ile Asp Thr Asp Ser Leu Gln Val Gly Lys Ala Tyr Leu Ile
        275                 280                 285

Gly Gly Arg Asp Met Lys Asn Val His Gly Leu Tyr Thr Gly Thr Thr
    290                 295                 300

Phe Asp Gln Gln His Ala Asn Phe Leu Ile Val Glu Thr Asp Arg Met
305                 310                 315                 320

His Arg Thr Leu Thr Val Ser Ala Glu Gln Leu Phe Ala Glu Glu Arg
                325                 330                 335

His Ile Val Asp Ile Glu Lys Arg Val Glu Gln Thr Glu Asp
            340                 345                 350

<210> SEQ ID NO 5
<211> LENGTH: 154
<212> TYPE: PRT
<213> ORGANISM: SPO1 Bacteriophage

<400> SEQUENCE: 5

Met Glu Lys Leu Pro Asn Thr Val Val Lys Val His Gly Glu Gly Met
1               5                   10                  15

Glu Ser Lys Leu Phe Pro Arg Lys Leu His Lys Asp Thr Asn Ser Ile
            20                  25                  30

Leu Arg Glu Asp Leu Val Ser Ala Cys Gln Glu His Ile Glu Ala Leu
        35                  40                  45

Val Glu Gly Met Ile Ala His Gly Asp Gly Arg Lys Val Ala Glu Leu
    50                  55                  60

Asp Thr Ser Thr Gln Tyr Tyr Trp His Leu Lys Leu Val Glu Tyr Thr
65                  70                  75                  80

Pro Ile Pro Gly Arg Thr Gln His Tyr Val Asp Leu Val Asp Gly Thr
                85                  90                  95

Asn Pro Asp Val Cys Tyr Phe Ser Leu Cys Asp Cys Ser Gly Asp Asn
            100                 105                 110

Ile Thr Asp Arg Arg Trp Ser Asn Met Val Lys Arg Leu Gln Asn Pro
        115                 120                 125

Glu Glu Asp Ile Ala Lys Thr Leu Arg Cys Tyr Phe Arg Gln Asp Ala
    130                 135                 140

Gly Met Pro Ser Trp Ile Glu Tyr Pro Gln
145                 150

<210> SEQ ID NO 6
<211> LENGTH: 88
<212> TYPE: PRT
<213> ORGANISM: SPO1 Bacteriophage

<400> SEQUENCE: 6
```

```
Met Arg Lys Phe Val Thr Thr Leu Thr Ala Ser Pro Arg Asn Lys Lys
1               5                   10                  15

Val Gly Asn His Arg Leu Glu Ile Ser Pro Phe Val Ser Leu Arg Arg
            20                  25                  30

Tyr Tyr Tyr Phe Asn Thr Ala Ile Cys Ile Glu Asn Pro Val Thr Arg
        35                  40                  45

Glu Phe Ala Ile Asp Asp Ser Tyr Gly Ser Leu Ser Thr Asn Gln Asn
    50                  55                  60

Cys Ala Gln Tyr Arg Gln Tyr Phe Ser Leu Gly Gly Tyr Lys Glu Val
65                  70                  75                  80

Ser Leu Glu Glu Ile His Ala Val
                85
```

```
<210> SEQ ID NO 7
<211> LENGTH: 90
<212> TYPE: PRT
<213> ORGANISM: SPO1 Bacteriophage

<400> SEQUENCE: 7

Met Ile Gln Leu Ser Glu Arg Gln Gln Asp Leu Leu Gln Val Ala Glu
1               5                   10                  15

Lys Tyr Glu Gln Cys His Ile Glu Phe Tyr Thr Ala Gln Ser Arg Leu
            20                  25                  30

Phe Gly Thr Glu Ile Met Gly Glu Val Val Lys Thr Ser Leu Gly Thr
        35                  40                  45

Leu Lys Ile Ala His Pro Glu Asp Leu Phe Glu Val Ala Leu Ala
    50                  55                  60

Tyr Leu Ala Ser Lys Lys Asp Ile Leu Thr Ala Gln Glu Arg Lys Asp
65                  70                  75                  80

Val Leu Phe Tyr Ile Gln Asn Asn Leu Cys
                85                  90
```

```
<210> SEQ ID NO 8
<211> LENGTH: 237
<212> TYPE: PRT
<213> ORGANISM: SPO1 Bacteriophage

<400> SEQUENCE: 8

Met Ala Lys Ser Asn Asn Val Tyr Val Val Asn Gly Glu Glu Lys Val
1               5                   10                  15

Ser Thr Leu Ala Glu Val Ala Lys Val Leu Gly Val Ser Arg Val Ser
            20                  25                  30

Lys Lys Asp Val Glu Glu Gly Lys Tyr Asp Val Val Val Glu Glu Ala
            35                  40                  45

Ala Val Ser Leu Ala Asp Thr Glu Glu Val Val Glu Glu Val Val Thr
    50                  55                  60

Glu Glu Glu Asp Ile Leu Glu Gly Val Glu Val Val Glu Asp Glu Glu
65                  70                  75                  80

Glu Glu Glu Ala Ala Glu Asp Val Glu Glu Pro Thr Ser Glu Glu Asp
                85                  90                  95

Ser Glu Asp Glu Trp Glu Glu Gly Tyr Pro Val Ala Thr Glu Val Glu
            100                 105                 110

Glu Asp Glu Asp Glu Glu Ile Glu Tyr Pro Glu Val Gly Asp Phe Glu
        115                 120                 125

Asp Glu Lys Ala Ile Lys Lys Tyr Ile Lys Gly Leu Thr Asp Glu Gln
    130                 135                 140
```

```
Leu Gln Ala Trp Cys Glu Leu Glu Gly Ala Glu Trp Val Glu Asn Glu
145                 150                 155                 160

His Arg Asn Ile Asn Arg Met Arg Met Ala Met Ala Ile Lys Ala Val
                165                 170                 175

His Phe Pro Glu Leu Ala Lys Lys Pro Ser Ser Lys Lys Lys Ser Lys
            180                 185                 190

Tyr Ala Glu Tyr Thr Thr Glu Glu Leu Val Glu Met Ala Ile Asp Asn
            195                 200                 205

Asn Val Glu Val Arg Asp Asp Lys Gly Asn Glu Arg Ile Leu Arg Met
210                 215                 220

Tyr Thr Ile Ile Ala Leu Arg Glu Ala Gly Leu Ile Ser
225                 230                 235

<210> SEQ ID NO 9
<211> LENGTH: 99
<212> TYPE: PRT
<213> ORGANISM: SPO1 Bacteriophage

<400> SEQUENCE: 9

Met Met Met Asp Lys Gln Val Glu Val Lys Lys His Tyr Pro Ile
1               5                   10                  15

Val Glu Asp Trp Ser Val Ile Val Ala Arg Lys Glu Asp Asp Cys Met
                20                  25                  30

Thr Val Thr Asp Ala Val Pro Phe Ile Leu Ala Gly Tyr Lys Asn Val
            35                  40                  45

Ser Tyr Glu Met Asp Asp Ile Val Val Leu Cys Ser Glu Pro Ile Gly
        50                  55                  60

Leu Thr Trp Glu Asp Val Arg Phe Leu Lys Asn His Glu Gly Ser Val
65                  70                  75                  80

Ser Phe Glu Glu Ile Gly Tyr Glu Asp Lys Ala Met Val Tyr His Val
                85                  90                  95

Asp Leu Gly

<210> SEQ ID NO 10
<211> LENGTH: 77
<212> TYPE: PRT
<213> ORGANISM: SPO1 Bacteriophage

<400> SEQUENCE: 10

Met Met Thr Glu Asp Gln Lys Phe Lys Tyr Leu Thr Lys Ile Glu Glu
1               5                   10                  15

Leu Glu Ala Gly Cys Phe Ser Asp Trp Thr Lys Glu Asp Ile Thr Gly
                20                  25                  30

Asp Leu Lys Tyr Leu Lys Lys Gly Ile Ile Glu Glu Ser Ile Glu Leu
            35                  40                  45

Ile Arg Ala Val Asn Gly Leu Thr Tyr Ser Glu Leu His Asp Phe
        50                  55                  60

Thr Gln Glu Ile Ile Glu Glu Leu Asp Ile Ser Pro Leu
65                  70                  75

<210> SEQ ID NO 11
<211> LENGTH: 94
<212> TYPE: PRT
<213> ORGANISM: SPO1 Bacteriophage

<400> SEQUENCE: 11

Met Asp Trp Thr Lys Met Thr Phe Met Gly Thr Val Asp Glu Val Lys
```

```
                1               5                  10                 15
Glu Ile Trp Asn Gly Leu Glu Glu Ala Gly Arg Leu Tyr Ala Val Trp
                    20                 25                 30

Leu Ser Asp Asp His Val Tyr Gly Ile Val Asp Val Asn Glu Glu Gly
                    35                 40                 45

Leu Phe Cys Leu Gly Trp Val Ser Asp Ile Ser Pro Glu Ser Leu Gln
            50                 55                 60

Asn Met Leu Gly Gly Ala Glu Leu Phe Glu Ser Tyr Glu Asp Val
65                  70                 75                     80

Leu Ser Glu His Gly Gly Ser Ile Ala Ile Arg Val Glu Val
                    85                 90
```

<210> SEQ ID NO 12
<211> LENGTH: 126
<212> TYPE: PRT
<213> ORGANISM: SPO1 Bacteriophage

<400> SEQUENCE: 12

```
Met Pro Tyr Ser Lys Ile Thr Val Pro Val Leu Val Gly Gly Gly Leu
1               5                   10                  15

Thr Glu Trp Asp Val Ile Asp Val Met Arg Glu Thr His Pro Pro Thr
                    20                  25                  30

Val Glu Asp Gln Tyr His Tyr His Thr Phe Asp Ser Met Gln Asn Arg
                35                  40                  45

Thr Ile Phe Val Leu Glu Asn Pro Leu Tyr Pro Asp Val Asp Lys Ile
            50                  55                  60

Pro Glu Lys Val Leu Gly Ile Ala Val Asp Ala Leu Glu Asp Met Leu
65                  70                  75                  80

Asp Asn Val Pro Val Glu Asp Leu Pro Val Thr Glu Gln Gly Asn
                    85                  90                  95

Val Lys Arg Phe Thr Thr Lys Leu Ala Ser Ile Val Phe Asp Val Phe
                100                 105                 110

Leu Ile Ile Pro Asp Phe Val Ser Val Thr Ala Lys Glu Glu
            115                 120                 125
```

<210> SEQ ID NO 13
<211> LENGTH: 117
<212> TYPE: PRT
<213> ORGANISM: SPO1 Bacteriophage

<400> SEQUENCE: 13

```
Met Ile Lys Ala Ala Val Thr Lys Glu Ser Leu Tyr Arg Met Asn Thr
1               5                   10                  15

Leu Met Glu Ala Phe Gln Gly Phe Leu Gly Leu Asp Leu Gly Glu Phe
                    20                  25                  30

Thr Phe Lys Val Lys Pro Gly Val Phe Leu Leu Thr Asp Val Lys Ser
                35                  40                  45

Tyr Leu Ile Gly Asp Lys Tyr Asp Asp Ala Phe Asn Ala Leu Ile Asp
            50                  55                  60

Phe Val Leu Arg Asn Asp Arg Asp Ala Val Glu Gly Thr Glu Thr Asp
65                  70                  75                  80

Val Ser Ile Arg Leu Gly Leu Ser Pro Ser Asp Met Val Val Lys Arg
                    85                  90                  95

Gln Asp Lys Thr Phe Thr Phe Thr His Gly Asp Leu Glu Phe Glu Val
                100                 105                 110

His Trp Ile Asn Leu
```

-continued

```
            115

<210> SEQ ID NO 14
<211> LENGTH: 23
<212> TYPE: PRT
<213> ORGANISM: SPO1 Bacteriophage

<400> SEQUENCE: 14

Met Asp Lys Leu Ala Ala Gly Gly Leu Tyr Leu Leu Phe Leu Leu Leu
1               5                   10                  15

Ala Gly Ile Ile Val Thr His
            20

<210> SEQ ID NO 15
<211> LENGTH: 131
<212> TYPE: PRT
<213> ORGANISM: SPO1 Bacteriophage

<400> SEQUENCE: 15

Met Ala Lys Ile Asn Lys Gly Tyr Val Ala Asn Phe Ile Glu Glu Asn
1               5                   10                  15

Gly Phe Pro Glu Gln Gly His Phe Glu Lys Lys Asp Leu Gln Ala
            20                  25                  30

Phe Tyr Lys His Leu Ser Thr Glu Gln Leu Glu Glu Trp Val Glu Leu
            35                  40                  45

Glu Gly Leu Glu Val Lys Asp Thr Asp Ser Asp Ser Ile Tyr Arg Met
        50                  55                  60

Arg Leu Cys Met Ala Ile Leu Tyr Leu Asn Phe Pro Lys Lys Thr Ala
65                  70                  75                  80

Gly Lys Lys Lys Ala Ser Pro Tyr Lys His Ile Ser Leu Glu Glu Leu
                85                  90                  95

Val Gln Met Ala Thr Asp Asn Asp Ile Glu Val Lys His Thr Asp Ser
            100                 105                 110

Asp Lys Ile Leu Arg Met Arg Thr Ile Met Ala Leu Lys Glu Ala Gly
        115                 120                 125

Lys Leu Gly
    130

<210> SEQ ID NO 16
<211> LENGTH: 158
<212> TYPE: PRT
<213> ORGANISM: SPO1 Bacteriophage

<400> SEQUENCE: 16

Met Thr His Phe Ile Ser Ile Ala Thr Tyr Ile Tyr Ala Leu Val Ser
1               5                   10                  15

Ala Gly Phe Ile Gly Gly Trp His Asp Glu Glu Ser Trp Ile Lys Asp
            20                  25                  30

Thr Glu Tyr Glu His Gly Gly Tyr His Met Ile Ile Asp Thr Pro Ala
            35                  40                  45

Val Val Asn Tyr Ser Leu Glu Tyr Gly Asn Tyr Gln Trp Ile Phe Gln
        50                  55                  60

Lys Tyr Met Lys Glu Gly Lys Val Thr Val Glu Arg Phe Tyr Arg Asn
65                  70                  75                  80

Ser Leu Asp Ile Pro Lys Glu Ile Leu Thr Asp Glu Ala Leu Ala Phe
                85                  90                  95

Ile Lys Asp Trp Asp Glu Asn Ala Asn Glu Tyr Glu Leu His Ala Gly
            100                 105                 110
```

```
Glu Gly Val Leu Tyr Phe Lys Tyr Glu Gly Glu Lys Gly Tyr Val
            115                 120                 125

Ile Pro Met Ala Tyr Ala Gly Glu Ile Met Phe Val Pro Asp Glu Asp
        130                 135                 140

Ala Glu Lys Ala Leu Glu Ile Ile Asn Ser Gln Lys Lys Tyr
145                 150                 155
```

<210> SEQ ID NO 17
<211> LENGTH: 218
<212> TYPE: PRT
<213> ORGANISM: SPO1 Bacteriophage

<400> SEQUENCE: 17

```
Met Arg Thr Tyr Trp Asn Val Ser Leu Asp Arg Ser Asn Gly Lys Arg
1               5                   10                  15

Phe Glu Arg Leu Val His Tyr Ile Cys Val Pro Ile Ile Ser Ile His
            20                  25                  30

His Ala Glu Asp Thr Ile Ser Met Thr Arg Lys Glu Val Gly His Leu
        35                  40                  45

Ala Glu Thr Ile Ala Asn His Ile Ile Leu Asp Ile Asn Gly Thr Tyr
    50                  55                  60

Arg Thr Phe Ser Val Asn Asp Ile Val His Cys Ser Leu Glu Lys Val
65                  70                  75                  80

Ile Thr Leu Glu Gly Asp Val Thr Asn Glu Phe Ile Asp Arg Leu Gln
                85                  90                  95

Ile Leu Val Asn Lys Glu Val Gln Gly Ser Gln Ser Thr Gln Gln Ser
            100                 105                 110

Leu Ser Ser Val Phe Glu Ser Thr Leu Glu Lys Tyr Asn Ser Pro Asp
        115                 120                 125

Asp Phe Ala Asp Tyr Leu Glu Glu Thr Glu Glu Val Asp Tyr Glu
    130                 135                 140

Asp Tyr Ser Leu Asp Asp Thr Ile Asp Ala Ile Ser Tyr Ala Leu Lys
145                 150                 155                 160

Thr Gln Glu Pro Val Gln Ala Glu Trp Cys Leu Leu Met Val Asp Val
                165                 170                 175

Tyr Thr Gly Thr Leu Thr Glu Val Thr Val Glu Thr Asp Lys Asp Lys
            180                 185                 190

Thr Leu Asp Ser Ile Leu Gly Lys Tyr Leu Glu Asn Gly Phe Glu Cys
        195                 200                 205

Val Ser Lys Lys Arg Leu Gly Glu Val Leu
    210                 215
```

<210> SEQ ID NO 18
<211> LENGTH: 46
<212> TYPE: PRT
<213> ORGANISM: SPO1 Bacteriophage

<400> SEQUENCE: 18

```
Met Val Ile Ile Lys Tyr Thr Thr Lys Thr Gln Pro Thr Pro Val Lys
1               5                   10                  15

Glu Met Phe Ile Ser Pro Gln His Tyr Ala Lys Trp Arg Ser His Met
            20                  25                  30

Gly Ser Lys Leu Thr Ser Val Lys Pro Ile Lys Gly Arg
        35                  40                  45
```

<210> SEQ ID NO 19

```
<211> LENGTH: 40
<212> TYPE: PRT
<213> ORGANISM: SPO1 Bacteriophage

<400> SEQUENCE: 19

Met Phe Lys Leu Leu Thr Leu Phe Lys Arg Asn Lys Ile Thr Ser Ala
1               5                   10                  15

Glu Glu Tyr Tyr Thr Gln Ala Ile His Ile Cys Glu Gln Phe Asp Arg
            20                  25                  30

Ser Thr Gln Lys Tyr Thr Ser Met
        35                  40

<210> SEQ ID NO 20
<211> LENGTH: 79
<212> TYPE: PRT
<213> ORGANISM: SPO1 Bacteriophage

<400> SEQUENCE: 20

Met Phe Lys Tyr Thr Asp Arg Ser Val Arg Gln Tyr Ile Glu Arg Gln
1               5                   10                  15

Gln Arg Ser Ala Met Leu Glu Gln Glu Gln Ala Glu Lys Asp Lys Lys
            20                  25                  30

Glu Arg Arg Lys Ala Gly Leu Leu Phe Phe Gly Thr Ile Val Val Leu
        35                  40                  45

Val Ala Val Ala Val Tyr Ile Val Pro Gln Ser Leu Asp Ala Met
    50                  55                  60

Trp His Glu Asn Tyr Glu Lys Pro Ala Gln Glu Ala Ala Arg Asn
65                  70                  75

<210> SEQ ID NO 21
<211> LENGTH: 113
<212> TYPE: PRT
<213> ORGANISM: SPO1 Bacteriophage

<400> SEQUENCE: 21

Met Thr Leu Phe Ile Ala Gly Val Thr Leu Glu Glu Val Arg Glu Ala
1               5                   10                  15

Thr Val Ser Ala Leu Phe Val Lys Leu Glu Gln Glu Lys Lys Ala Leu
            20                  25                  30

Tyr Leu Gly Ala Gly Ser Glu Asp Ser Leu Asn Leu Cys Lys Ser Thr
        35                  40                  45

Leu Asp Lys Val Gln Glu Asp Tyr Pro Leu Asp Met Glu Lys Asp
    50                  55                  60

Tyr Leu Arg Asp Leu Leu Gln Phe Trp Leu Ser Arg Leu Phe Leu Gly
65                  70                  75                  80

Asp Gly Phe Glu Gly Glu Ile Pro Asp Ser Ser Glu Asp Leu Arg Arg
            85                  90                  95

Thr Ala Thr Ala Phe Thr Tyr Thr Ala Ala Ile Arg His Tyr Cys
        100                 105                 110

Met

<210> SEQ ID NO 22
<211> LENGTH: 35
<212> TYPE: PRT
<213> ORGANISM: SPO1 Bacteriophage

<400> SEQUENCE: 22

Met Thr Leu Ala Gly Tyr Arg Val Asp Ser Cys Asn Gly Cys Gly Lys
1               5                   10                  15
```

```
Ala Tyr Leu Val Gly Glu Ser His Asp Arg Lys Lys Cys Ala Glu Cys
            20                  25                  30

Ala Ser Lys
        35

<210> SEQ ID NO 23
<211> LENGTH: 56
<212> TYPE: PRT
<213> ORGANISM: SPO1 Bacteriophage

<400> SEQUENCE: 23

Met Lys Lys Arg Tyr Lys Val Thr Ala Leu Phe Glu Asp Gly Thr Ser
1               5                   10                  15

Gln Cys Leu Val Val Gly Asn Phe Ser Ser Pro Thr Asn Ala Trp Cys
            20                  25                  30

Ala Ala Met Arg Asn Leu Thr Pro Glu Gly Ile Ala Arg Val Gln His
            35                  40                  45

Tyr Asn Val Glu Glu Ile Ser Lys
    50                  55

<210> SEQ ID NO 24
<211> LENGTH: 72
<212> TYPE: PRT
<213> ORGANISM: SPO1 Bacteriophage

<400> SEQUENCE: 24

Leu Asn Gln Val Glu Val Leu Arg Glu Glu Tyr Val Glu Gly Tyr Val
1               5                   10                  15

Val Gln Met Trp Arg Arg Asn Pro Ser Asn Ala Pro Val Ile Glu Val
            20                  25                  30

Phe Thr Glu Asp Asn Leu Glu Glu Gly Ile Ile Pro Glu Tyr Val Thr
            35                  40                  45

Ala Asn Asp Asp Thr Phe Asp Arg Ile Val Asp Ala Val Glu Phe Gly
        50                  55                  60

Tyr Leu Glu Glu Leu Glu Leu Val
65                  70
```

ANTIMICROBIAL PROTEINS FROM THE SPO1 BACTERIOPHAGE

CROSS-REFERENCE TO RELATED APPLICATIONS

This Application claims priority to U.S. provisional application 60/457,287 filed on Mar. 25, 2003.

STATEMENT REGARDING FEDERALLY SPONSORED RESEARCH OR DEVELOPMENT

The present invention may have been developed with funds from the United States Government. Therefore, the United States Government may have certain rights in the invention.

REFERENCE TO A COMPACT DISK APPENDIX

A Sequence Listing, including SEQ ID NO: 1 to 24, is submitted with this application.

FIELD OF THE INVENTION

The invention relates to proteins from the SPO1 bacteriophage, genes encoding same, and their use in arresting bacterial metabolism. Further, the present invention relates to a method of treating infected patients through the introduction of proteins, peptide fragments of the proteins or peptidomimetics, or genes encoding same into the bacteria infecting the patient.

BACKGROUND OF THE INVENTION

Viruses are obligate parasites that use the host's mechanisms for expressing their genes and propagating themselves. Bacteriophage, or "phage" for short, are viruses that infect bacteria. Phage have a host range that is often fairly narrow, infecting a single species or a group of related species.

Some bacteriophage, such as T4, always kill their hosts within a short time after infection—they are called LYTIC phages. Others, such as Lambda, can also establish themselves in a dormant form within the cell and be maintained stably over many generations—they are called LYSOGENIC phages. On infection lysogenic phages have a choice between a lytic cycle or to establish lysogeny.

In a lysogenic cycle, the phage integrates into the host chromosome at a specific point using a site-specific recombination process. The expression of most phage genes is shut down by a repressor and the phage genome can be replicated as part of the host chromosome. Under certain conditions, usually involving host stress, the genes get switched on again and the phage genome is excised from the chromosome, replicated and new phage particles are released by lysing the cell.

After their discovery early in the 20th century, phage were widely used to treat various bacterial diseases in people and animals. After an enthusiastic beginning, poorly designed research protocols and the development of antibiotics ended most phage therapy research in the West. However, phage therapy continued in Poland and the former Soviet Union for decades and the Eastern European experience should serve to bootstrap the technology into the U.S. Thus, although there are few, if any, clinical trials underway in the U.S., the technology is reasonably well developed and its advantages and limitations are well understood.

The alarming rise in antibiotic resistance in bacteria is leading to a resurgence of interest in bacteriophage research. In fact several companies exist that are dedicated to the realization of phage therapy. The Eliava Institute of Bacteriophage, Microbiology & Virology in the Republic of Georgia has been an international leader in phage therapy for over 70 years and has the world's largest collection of therapeutic phages. Other companies including Exponential Biotherapies, Inc. of New York; Intralytix, Inc. in Maryland; Phage Therapeutics International, Inc. (PhageTx) of British Columbia; Biophage, Inc. of Quebec; and PhageTech, Inc. of Quebec are developing commercial phage therapies.

The limitations and advantages of phage therapy are listed by Elizabeth Kutter of Evergreen State College at www.evergreen.edu/phage/phagetherapy.html. Her lists are worth iterating here in order to understand the potential and limitations of phage therapy. The limitations include: 1) Paucity of understanding of the heterogeneity and ecology of both the phages and the bacteria involved; 2) Failure to select phages of high virulence against the target bacteria before using them in patients; 3) Use of single phages in infections that involve mixtures of different bacteria; 4) Emergence of resistant bacterial strains, which can occur by selection of resistant mutants (a frequent occurrence if only one phage strain is used against a particular bacterium) or by lysogenization (if temperate phages are used); 5) Failure to appropriately characterize or titer phage preparations, some of which were totally inactive; 6) Failure to neutralize gastric pH prior to oral phage administration; 7) Inactivation of phages by both specific and nonspecific factors in body fluids; 8) Liberation of endotoxins as a consequence of widespread lysis of bacteria in the body (this is called the Herxheimer reaction); and 9) Failure to identify the bacterial pathogens involved necessitated by the relative specificity of phage therapy.

The advantages of phage therapy include: 1) They are self-replicating and self-limiting, because they multiply only as long as sensitive bacteria are present and then are gradually eliminated; 2) They target specific bacteria, causing less damage to the normal microbial balance in the body; 3) Phage can often be targeted to receptors on the bacterial surface that are involved in pathogenesis, so that any resistant mutants are attenuated in virulence; 4) Few side effects have been reported for phage therapy; 5) Phage therapy would be particularly useful for people with allergies to antibiotics; 6) Appropriately selected phages can easily be used to prevent bacterial disease in people or animals at times of exposure, or to sanitize hospitals and help protect against hospital-acquired infections; 7) Phage can be prepared fairly inexpensively and locally, facilitating their potential applications to underserved populations; 8) Phage can be used independently or in conjunction with other antibiotics to help reduce the development of bacterial resistance; and 9) Multiple delivery means are available, including noninvasive means like topical application, oral administration, and inhalation.

One lytic phage of long time interest to our laboratory is called "SPO1." SPO1 has a linear dsDNA genome of 140 kb, and its host is the bacterium *Bacillus subtilis*. Early in SPO1 infection of *B. subtilis*, the synthesis of most host-specific molecules is replaced by the corresponding phage-specific biosynthesis. Subversion of the host machinery is accomplished primarily by a cluster of early genes in the SPO1 terminal repeat in an 11.5-kb "host-takeover module." The module includes 24 genes, tightly packed into 12 operons driven by the previously identified early promoters PE1 to PE12.

The 24 genes are smaller than average, with half of them having fewer than 100 codons. Most of their inferred products show little similarity to known proteins, although zinc finger, trans-membrane, and RNA polymerase-binding domains were identified therein. Transcription-termination and RNase III cleavage sites were identified in the nucleotide sequence as well. We have placed most of these 24 genes into an inducible *B. subtilis/E. coli* shuttle vector and introduce them here for use in phage therapy and as antimicrobial agents.

BRIEF SUMMARY OF THE INVENTION

As used herein "tightly regulated inducible promoter" is an inducible promoter that does not express detectable levels of protein in the absence of the inducing agent. Detectable levels of protein expression could be indicated by inhibition of bacterial host cell growth. In other words, the promoter is not "leaky" to a degree sufficient to prevent cloning of the gene in the host cell.

As used herein "recombinant" is relating to, derived from, or containing genetically engineered material.

"% identity" is calculated over the entire length of a specified sequence, thus short local alignments with a claimed sequence are not relevant (e.g., % identity=number of aligned residues/length of reference sequence). Alignments are preformed using BLAST (Basic Local Alignment Search Tool) homology alignment as described by Tatusova and Madden (1999). The default parameters are used, except the filters are turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=-3; r reward for nucleotide match [Integer] default=1; e expect value [Real] default=10; W wordsize [Integer] default=11 for nucleotides, 3 for proteins; y Dropoff (X) for blast extensions in bits (default if zero) default=20 for BLASTN, 7 for other programs; X dropoff value for gapped alignment (in bits) 30 for BLASTN, 15 for other programs; Z final X dropoff value for gapped alignment (in bits) 50 for BLASTN, 25 for other programs. This program is available online at http://www.ncbii.nlm.nih.gov/BLAST/.

The invention provides expression vectors encoding a protein comprising a sequence selected from the group consisting of SEQ ID NO: 1–24, wherein the expression of the protein is controlled by an inducible promoter. The transcription must be under sufficiently tight control so as to allow the vector to be propagated in the host cell.

The invention also provides a method of designing peptidomimetic anti-bacterial drugs comprising preparing proteins of SEQ ID NO: 1 to 24 or variants with at least 95% identity over the entire length of the specified sequence by recombinant or synthetic means (e.g., peptide synthesis), determining their three-dimensional structures, and using the three-dimensional structure as the basis for designing peptidomimetic small molecules to be tested for anti-bacterial activity.

Methods of treating a bacterial infection in a warm blooded animal in need thereof are also provided. The methods require the direct in vivo delivery of an antimicrobial protein as described above, in an amount effective to kill bacteria, or delivery of a peptidomimetic small molecule having the bactericidal activity of the protein. Alternatively, the protein can be indirectly delivered by a bacteriophage that encodes said protein. Beneficially, the proteins of the invention do not lyse the bacteria, and are of particular use where an infection is halted without cell lysis and the concomitant release of bacterial toxins.

BRIEF DESCRIPTION OF THE DRAWINGS

FIG. 1. Shutoff of Host RNA Synthesis. At various times after infection at 30° C., cultures were pulse-labeled with [5-$^3$H] uridine. Single mutants 50- and 51- had no significant effect (data not shown), showing that both gene products, GP50 and GP51, contribute to the activity of GP50/51 ("GP" refers to "gene product" throughout). Each data point in such an experiment represents the sum of host and phage RNA synthesis.

FIG. 2. Shutoff of Host DNA Synthesis. At various times after infection at 30° C., cultures were pulse-labeled with [methyl-$^3$H] thymidine. Only host DNA synthesis was assayed in such an experiment, since SPO1 incorporates hmUra into its DNA in place of thymine.

FIG. 3. Shutoff of Host RNA Synthesis. Host and phage RNA synthesis were monitored as described for 39-, 40-, and 39-40- SPO1.

FIG. 4. Shutoff of Host DNA Synthesis. Host DNA synthesis was monitored in 39-, 40-, and 39-40- SPO1.

FIG. 5. Gene-Specific Expression Patterns. Cultures infected with wild-type SPO1, mutant 28-, or triple mutant 44-50-51- were harvested at 5, 15, or 25 minutes after infection a 30° C. Triangles represent wild-type; squares represent the 28-mutant; and circles the triple mutant 44-50-51-.

FIG. 6. Differential Effects of Mutations on Immediate-Early, Delayed-Early, and Middle Transcription. Cultures were infected with wild-type SPO1, mutant 44-, double mutant 50-51-, or triple mutant 44-50-51-. The numbers at the top represent the gene or genes present in that spot on the dot blot. The gene categories are indicated across the top. Gene 27 falls under both middle and delayed-early categories.

FIG. 7A. Distinguishable Effects of Genes 50 and 51 in the presence of the 44-mutation. Rates of RNA synthesis were measured by pulse-labeling with [5-$^3$H]uridine.

FIG. 7B. Distinguishable Effects of Genes 50 and 51 in the absence of the 44-mutation. Rates of RNA synthesis were measured by pulse-labeling with [5-$^3$H]uridine.

FIG. 8. Expression of SPO1 GP44 in *E. coli*. Cells of *E. coli* strain DH5(pPW27), which expresses SPO1 gene 44 from an IPTG-inducible promoter, were transformed either with vector pACYC177 or with plasmid pPW40, in which the mutant rpoB gene had been cloned in pACYC177. Aliquots of the two cultures were induced by adding 0.2 mM IPTG at time 0, and were assayed for viable cells at various times thereafter, by plating on media lacking IPTG. Open symbols, no IPTG; Closed symbols, 0.2 mM IPTG added at time 0; Squares, mutant rpoB; and Circles, no mutant rpoB. Viable cell count is expressed in cells/ml×$10^{-6}$.

FIG. 9. Effect of Gene 40, Gene 44, Gene 50 and Gene 51 on Phage DNA Synthesis.

FIG. 10. Effect of Gene 44, Gene 50 and Gene 51 on Single Step Growth Curves.

DETAILED DESCRIPTION OF THE INVENTION

Figure 11:
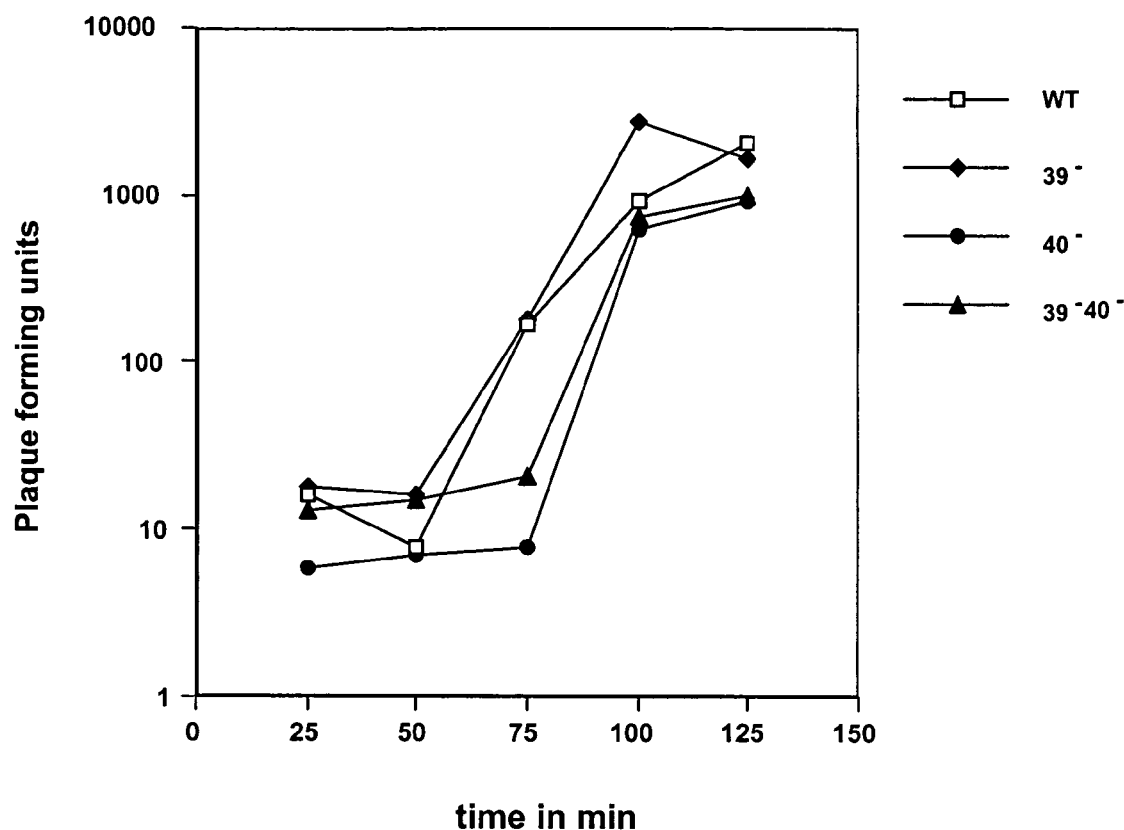
FIG. 11. Effect of Gene 39 and Gene 40 on Single Step Growth Curves.

The early gene region of the terminal redundancy of SPO1 is found at GenBank Acc. No. AF031901. It is a linear 11500 bp dsDNA, where 5-hydroxyniethyluracil (hmUra) is used instead of thymine as the base-pairing partner for adenine, and T's in the GenBank sequence represent hmUra. There are 24 small proteins encoded therein. The 24 genes are arranged in 12 operons, each of which includes between one and 4 genes. Genes 51 and 50 constitute one operon; gene 44 is the only gene in its operon; genes 37–40 are all in one operon. Genes 37–49 are transcribed rightward and 60–50 are transcribed leftward, which is why the latter are expressed in reverse numerical order. The genes encoded proteins are listed in Table 1.

TABLE 1

Anti-bacterial proteins from SPO1

| Gene Name | SEQ ID NO: | Peptide Sequence |
|---|---|---|
| 37 | 1 | MSDVIIPFLTSAVTAFIVAYLLDRWYIKRRR |
| 38 | 2 | MSVQIKHGNKTFVVDPSGDVKEGSYVLYLYEYRLGEVDVGRVSEVANDGRLYLDGPGVIVTLDQ PFILLKEVVEEEEDEDDRIDAEFHNDPLLRKLENTTEKLTPEETQLAQWTTMTRVFSHDLKKGI PYAIKHKNSGNILYGLYSGLLNPVTALFRHLNEESKISIEQLKSGLIEIYEVVEDEEESIWN |
| 39 | 3 | MELNLDIYVDYKDKRYKAEGYYGPSVGDLVLIFMDMELEGATVQEVARIEGSEIHLRTPNGNEP SYRYMGQYLILKPYGSSDPRDGILVHEDVQYVRVDAQAMPGDLIEALEPNKLPFSGKRFKYRPA VLEVEYVLTKDEQVLQLENGKSYSGAYRVLIPRMGVLPPKTHIYTTHKHVFMEDVFVLGNSYEL SSPNDVEMTPIHAVFTGFSKNRDEAIFVNPYYNDDGVTGTMITVSDLLTGKWDITPLVPKKGV |
| 40 | 4 | MHIYTYWGLKYVPSNSTMVAKEGDLILLGNEVHKVVKVLHRFRNITDLQITNWKGTETRYNLHV TEYKVLVPYDTHKEENEAMSDSLITHNGKDYVLCKIPARVGDLIRTEDKRVWEVLQKSKDGLVL YNEEKGEQRSAVYSEIGPYHVLVPRDTDTHTPTREELAAVIMNKAFTRTETQDSQEDTGTHKGL GLTGTDLYHSLRDLDAKVQSGYYTATENEEDVKSEIEATKKHMKAVKESGKTVNDYRKEENTKR CKLKALTNKFNRLFLKSVIDTDSLQVGKAYLIGGRDMKNVHGLYTGTTFDQQHANFLIVETDRM HRTLTVSAEQLFAEERHIVDIEKRVEQTED |
| 41 | 5 | MEKLPNTVVKVHGEGMESKLFPRKLHKDTNSILREDLVSACQEHIEALVEGMIAHGDGRKVAEL DTSTQYYWHLKLVEYTPIPGRTQHYVDLVDGTNPDVCYFSLCDCSGDNITDRRWSNMVKRLQNP EEDIAKTLRCYFRQDAGMPSWIEYPQ |
| 42 | 6 | MRKFVTTLTASPRNKKVGNHRLEISPFVSLRRYYYFNTAICIENPVTREFAIDDSYGSLSTNQN CAQYRQYFSLGGYKEVSLEEIHAV |
| 43 | 7 | MIQLSERQQDLLQVAEKYEQCHIEFYTAQSRLFGTEIMGEVVKTSLGTLKIAHPEEDLFEVALA YLASKKDILTAQERKDVLFYIQNNLC |
| 44 | 8 | MAKSNNVYVVNGEEKVSTLAEVAKVLGVSRVSKKDVEEGKYDVVVEEAAVSLADTEEVVEEVVT EEEDILEGVEVVEDEEEEEAAEDVEEPTSEEDSEDEWEEGYPVATEVEEDEDEEIEYPEVGDFE DEKAIKKYIKGLTDEQLQAWCELEGAEWVENEHRNINRMRMAMAIKAVHFPELAKKPSSKKKSK YAEYTTEELVEMAIDNNVEVRDDKGNERILRMYTIIALREAGLIS |
| 45 | 9 | MMMDKQVEEVKKHYPIVEDWSVIVARKEDDCMTVTDAVPFILAGYKNVSYEMDDIVVLCSEPIG LTWEDVRFLKNHEGSVSFEEIGYEDKAMVYHVDLG |
| 46 | 10 | MMTEDQKFKYLTKIEELEAGCFSDWTKEDITGDLKYLKKGIIEESIELIRAVNGLTYSEELHDF TQEIIEELDISPL |
| 47 | 11 | MDWTKMTFMGTVDEVKEIWNGLEEAGRLYAVWLSDDHVYGIVDVNEEGLFCLGWVSDISPESLQ NMLGGGAELFESYEDVLSEHGGSIAIRVEV |
| 48 | 12 | MPYSKITVPVLVGEGLTEWDVIDVMRETHPPTVEDQYHYHTFDSMQNRTIFVLENPLYPDVDKI PEKVLGIAVDALEDMLDNVPVEDLPVTEEQGNVKRFTTKLASIVFDVFLIIPDFVSVTAKEE |
| 49 | 13 | MIKAAVTKESLYRMNTLMEAFQGFLGLDLGEFTFKVKPGVFLLTDVKSYLIGDKYDDAFNALID FVLRNDRDAVEGTETDVSIRLGLSPSDMVVKRQDKTFTFTHGDLEFEVHWINL |
| 50 | 14 | MDKLAAGGLYLLFLLLAGIIVTH |
| 51 | 15 | MAKINKGYVANFIEENGFPEQGHFEEKKDLQAFYKHLSTEQLEEWVELEGLEVKDTDSDSIYRM RLCMAILYLNFPKKTAGKKKASPYKHISLEELVQMATDNDIEVKHTDSDKILRMRTIMALKEAG KLG |
| 52 | 16 | MTHFISIATYIYALVSAGFIGGWHDEESWIKDTEYEHGGYHMIIDTPAVVNYSLEYGNYQWIFQ KYMKEGKVTVERFYRNSLDIPKEILTDEALAFIKDWDENANEYELHAGEGVLYFKYEGEEKGYV IPMAYAGEIMFVPDEDAEKALEIINSQKKY |
| 53 | 17 | MRTYWNVSLDRSNGKRFERLVHYICVPIISIHHAEDTISMTRKEVGHLAETIANHIILDINGTY RTFSVNDIVHCSLEKVITLEGDVTNEFIDRLQILVNKEVQGSQSTQQSLSSVFESTLEKYNSPD DFADYLEETEEEVDYEDYSLDDTIDAISYALKTQEPVQAEWCLLMVDVYTGTLTEVTVETDKDK TLDSILGKYLENGFECVSKKRLGEVL |

TABLE 1-continued

Anti-bacterial proteins from SPO1

| Gene Name | SEQ ID NO: | Peptide Sequence |
|---|---|---|
| 54 | 18 | MVIIKYTTKTQPTPVKEMFISPQHYAKWRSHMGSKLTSVKPIKGGR |
| 55 | 19 | MFKLLTLFKRNKITSAEEYYTQAIHICEQFDRSTQKYTSM |
| 56 | 20 | MFKYTDRSVRQYIERQQRSAMLEQEQAEKDKKERRKAGLLFFGTIVVLVAVVAVYIVPQSLDAM WHENYEKPAQEAARN |
| 57 | 21 | MTLFIAGVTLEEVREATVSALFVKLEQEKKALYLGAGSEDSLNLCKSTLDKVQEDYPLDDMEKD YLRDLLQFWLSRLFLGDGFEGEIPDSSEDLRRTATTAFTYTAAIRHYCM |
| 58 | 22 | MTLAGYRVDSCNGCGKAYLVGESHDRKKCAECASK |
| 59 | 23 | MKKRYKVTALFEDGTSQCLVVGNFSSPTNAWCAAMRNLTPEGIARVQHYNVEEISK |
| 60 | 24 | LNQVEVLREEYVEGYVVQMWRPNPSNAPVIEVFTEDNLEEGIIPEYVTANDDTFDRIVDAVEFG YLEELELV |

Single Step Growth Experiment: Cells of CB10 were infected at an MOI of about 0.1 at 30° C. The infected cultures were diluted through anti-SPO1 antibody and plated on CB313 lawns at 25 minute intervals. Plaque forming units (Pfu) were counted and plotted against time.

SDS-PAGE: Cultures of CB10 were infected with appropriate strains of SPO1 at an MOI of 5, and shaken at 30° C. At various times, aliquots were pulse labeled for 2 minutes with ($^{35}$S) Met-Cys. Extracted proteins were subjected to SDS-PAGE, and autoradiographs were prepared.

RNA preparation: Cultures in VY medium were harvested at the indicated times after infection, as described previously (Wei and Stewart, 1993). The RNA was purified using the QIAGEN® RNEASY® Mini Kit, following the manufacturer's protocol.

Dot blots: PCR products carrying a particular gene or genes were denatured by incubating for 15 minutes at 37° C. in 0.2M NaOH. 10 ng of DNA in 2 μl were spotted onto positively charged nylon membranes, AMERSHAM® HYBOND™ N+, and bound by UV crosslinking. Each 11 cm×5 cm membrane held an array of about 23 spots. The PCR fragments included all, or nearly all, of the specified gene or genes, except for gene 31 which included only the first exon.

Hybridization: For each RNA preparation, a 1.0 μg aliquot was labeled with alkaline phosphatase, using the AMERSHAM® ALKPHOS™ Direct Labeling and Detection Kit. The entire labeled preparation was hybridized to one membrane carrying a dot blot array, using the hybridization buffer defined in the kit. Hybridization was at 60° C. for two hours in a ROBBINS® Model 400 hybridization incubator rotating at about 4 rpm. Wash buffers were as defined in the kit, with the primary wash at 65° C. and the secondary wash at room temperature. Detection of hybridized RNA used the AMERSHAM® CDP-STAR™ Chemiluminescent Detection Reagent, following procedures from the kit. The alkaline phosphatase catalyses decomposition of dioxetane with emission of light, which is detected on film, using HYPERFILM ECL™ from AMERSHAM®. All hybridizations were done under the same conditions, without attempting to identify optimal conditions for each gene, and we have not made independent measurements of the concentrations of the various transcripts or of their intrinsic hybridization efficiencies. Thus, gene-to-gene differences in the absolute amount of signal detected could be due to differences in intrinsic hybridization or labeling efficiency. Conclusions were drawn only from comparisons between signal intensities for the same gene under different conditions.

Densitometry: The intensities of the dot-blot signals were measured with a MOLECULAR DYNAMICS™ computing densitometer. Positions at which no spot was visible on the film gave intensity values ranging from −20 to +20. Some spots that were faintly visible gave intensity readings less than 20, which are reported as measured, with the recognition that they represent only approximations of the actual value. Spots not visible on film are reported as 0. Intensity values as high as 1700 were within the linear dose-response range. Where undiluted samples gave values beyond the linear range, we measured hybridization by diluted samples, and corrected for the dilution factor and the experiment-to-experiment difference in hybridization efficiency Pulse Labeling: Rates of synthesis of host and phage RNA or protein were measured in C4 medium as described previously (Wei and Stewart, 1993), by pulse-labeling for 5 minutes with [5-$^{3}$H]uridine, or [4,5-$^{3}$H]leucine, precipitating with TCA, and counting the precipitate. Since SPO1 DNA contains hmUra in place of thymine, host DNA synthesis could be measured independently by pulsing with [methyl-$^{3}$H]thymidine. Phage DNA synthesis was measured by pulsing with [2,8-$^{3}$H]adenine, and measuring alkali-stable, TCA-precipitable counts. Pulsing with [2,8-$^{3}$H]adenine measures host as well as phage DNA synthesis, but most host DNA synthesis has been shut off by the time that phage replication begins, even in mutant infections, so incorporation of label after 12 minutes is overwhelmingly into phage DNA. The time given for each pulse is the time at which the pulse began.

Mutagenesis: Cloned genes were mutated using the STRATAGENE® QUIKCHANGE® kit. In each case, a nonsense codon was substituted for the first or second lysine codon (or for the first leucine codon in the case of gene 37) (codons 9, 10, 14, 10, 3, 11, 7, 3, 3, and 3 for genes 37, 38, 39, 40, 44, 45, 46, 50, 51 and 56, respectively), and the mutants were propagated on a suppressor strain (CB313) which inserts lysine at nonsense codons. Each mutagenized plasmid was allowed to recombine with superinfecting SPO1. Recombinant progeny were identified by plaque-lift hybridization, using the AMERSHAM ECL™ 3'-oligo labeling and detection kit, and allowed to segregate pure mutant strains. Multiple mutants were produced by successive recombination with the appropriate mutagenized plasmids and all genotypes were confirmed by DNA sequencing. The first 8 nucleotides of gene 50 overlap the last 8 nucleotides of gene 51, and the gene 50 mutation destroys the termination codon of gene 51, apparently permitting translation of gene 51 to run on for about 30 more amino acids, beyond its normal 151. Thus, definitive conclusions about the role of GP50 could not be made from single mutants in which only gene 50 was mutated. The gene 28 mutant was derived from mutant F21, initially described by Okubo et al. (1972), by 5 successive back crosses to wild-type SPO1. We have previously called it sus28-1 and our lab bookkeeping lists it as F21(5).

Identification of Immediate-Early, Delayed-Early, and Middle Genes: Expression of specific genes was measured by dot blot hybridization and densitonmetry. FIG. 5 shows the expression pattern of the known early genes and several representative middle genes, in the wild-type or when altered by either the 28- mutation or the 44-50-51- triple mutant. The 28-mutation inactivates the middle gene-specific sigma, permitting identification of middle gene activity. Note that different genes are expressed on different scales, as the absolute level of expression varies widely from gene to gene. The densitometric values for each gene are plotted as a function of time after infection. In each graph, the number in the upper left corner indicates the gene whose activity is plotted. Where an operon of more than one gene was assayed, the graph is labeled with the number of the first gene in the operon. This applies to operons 37–39, 45–46, 48–49, 51–50, 55–53, 58–56, and 60–59. To a first approximation, the immediate-early genes have been arranged from top to bottom in order of increasing activity. Gene 27 could have been displayed with either the delayed-early or the middle genes.

Genes 31 and TF1 were previously known to be middle genes (Greene et al., 1984; Scarlato and Gargano, 1992). The others are now identified as immediate-early genes (41–51 and 53–60), delayed-early genes (27, 28, and 37–40), or middle gene (52), on the basis of expression time in wild-type infection and of the GP28-dependence of their expression. Gene 27 had characteristics of both delayed-early and middle genes. Genes 48–49 also showed substantial GP28-dependent expression at late times (data not shown).

For FIG. 6, cells were harvested 15 minutes after infection at 30° C. RNA was prepared, labeled, hybridized to dot blots, and detected on film. The films were scanned using the UMAX® VISTA SCAN™ program with a UMAX® ASTRA 1220S™ scanner. A 25×25 pixel square surrounding each spot was copied and pasted into the grid displayed.

EXAMPLE 1

Antimicrobial Activity

For analysis of antimicrobial activity we first cloned most of the 24 host-takeover genes (genes 37–60) singly or in multiple gene combinations into a B. subtilis/E. coli shuttle vector (pPW19) under control of an IPTG-inducible promoter (Wei and Stewart, 1993). Certain genes and gene combinations were not clonable using this vector system, suggesting that these genes are highly toxic, and that the small amount of leaky expression that occurs, even without induction, is sufficient to kill the bacteria. These remaining genes are being cloned using expression vectors with more tightly regulated promoters, such as pJONEX4 (Sayers, 1996), pET101, or pX (Kim et al., 1996). The transformed E. coli and B. subtilis were used to determine the antimicrobial activity, if any, of the cloned genes. The effect of induction on bacterial growth and viability was measured both in liquid medium and by colony formation. Definitive establishment of lethality was shown by loss of the ability to form colonies even after removal from the inducing agent. Indication of probable lethality was based on total inability to form colonies under inducing conditions. Data obtained to date are summarized in Table 2, and discussed in more detail below.

TABLE 2

Summary of Lethality Data

| Gene | E. coli | B. subtilis |
| --- | --- | --- |
| 37 | Lethal * | No data |
| 38 | Highly toxic | No effect ** |
| 39 | Lethal | No data |
| 38/39 | Lethal | Lethal * |
| 40 | Mildly Toxic | Inconsistent |
| 38/39/40 | Lethal * | No data |
| 41 | Mildly Toxic | Lethal * |
| 42 | No effect | No effect |
| 43 | Indeterminate | Indeterminate |
| 44 | Lethal | Lethal |
| 51 | Lethal | Lethal |
| 50/51 | Lethal | Lethal |
| 44/50/51 | Highly Lethal | No data |
| 45 | Toxic | Mildly Toxic |
| 46 | Lethal | Mildly Toxic |
| 45/46 | Highly Toxic | Lethal |
| 47 | No effect | No effect |
| 48 | Strongly Toxic | Strongly Toxic |
| 49 | No data | No data |
| 48/49 | Non-Toxic ** | No data |
| 52 | Lethal | Not tested |
| 53/54/55 | Toxic | Toxic |
| 52/53/54/55 | Toxic | Toxic |
| 56 | Mildly toxic | Lethal |
| 57 | Mildly toxic | No effect |
| 58 | Mildly toxic | No effect |
| 56/57/58 | Lethal | Lethal |
| 59/60 | Toxic ** | Lethal ** |

* Lethality conclusion based on failure to clone, when appropriate controls cloned readily;
** Data not conclusive.

Genes 37–40: Fragments carrying either of genes 37 or 39 could not be cloned in pPW19 in the expressed orientation, although each was cloned in the opposite orientation, suggesting that expression of each of these clones is lethal, even at the low level of expression without induction. Gene 39 was cloned in a more tightly controlled expression vector, and its expression was lethal.

Expression of gene 40 by itself was only mildly toxic to either E. coli or B. subtilis. However, a plasmid expressing the triplet combination 38/39/40 could not be cloned in E. coli, except in one case where spontaneous integration of insertion sequence IS-1 had inactivated gene 40. In this plasmid, expression of the remaining wild-type genes 38/39 was lethal to E. coli. The same plasmid could not be transformed into B. subtilis, suggesting that even the uninduced level of 38/39 expression is lethal to B. subtilis. The fact that gene 40 had to be inactivated to permit cloning in E. coli suggests that GP40 reinforces the lethal activity of GP38 and GP39.

Mutational analysis in Example 2 (FIG. 4) shows that GP40 is essential for normal shutoff of host DNA synthesis, and that GP39 acts to restrain that activity of GP40. Mutational analysis (FIG. 3) also shows that both 39 and 40 are required for normal shutoff of host RNA and protein synthesis. The 38⁻ mutation was also deficient in shutoff of host DNA, RNA, and protein synthesis. Mutants inactivating gene 37 have also been isolated, but results with them are thus far inconclusive.

Gene 41: Expression of gene 41 has only a mild effect on *E. coli*, but the plasmid carrying it could not be transformed into *B. subtilis*, suggesting that the low level of expression without induction is lethal to *B. subtilis*. The gene has apparently been cloned in *B. subtilis*, using a more tightly controlled vector, but experiments with that clone are thus far inconclusive. A mutation inactivating the gene is being isolated.

Genes 42 and 43: Gene 42 showed no toxic effect on either bacterium, and results on gene 43 were too inconsistent to permit any conclusion.

Gene 44: Expression of gene 44 was shown to be lethal to both *B. subtilis* and *E. coli*. FIG. 8 shows an example of killing of *E. coli* by expression of SPO1 gene 44. In cells growing in liquid medium, expression of the cloned gene 44 was induced at time 0. At subsequent times, the number of cells remaining viable was measured by plating in the absence of inducer. More than 99% of the cells were killed within three hours. Similar experiments showed the lethal effect of gene 39, gene 56 and two-gene operons 45/46 and 50/51.

Genes 44, 50, and 51: Expression of either gene 44 or 51 alone is lethal to either *B. subtilis* or *E. coli*, inhibiting DNA, RNA, and protein synthesis. Adding gene 50 to the 51 clone increases its lethal efficiency, as does combining all 3 genes in a single clone. An *E. coli* mutant resistant to GP44 has a mutant rpoB gene, suggesting that the cellular target for GP44 is the bacterial RNA polymerase. Mutants resistant to genes 51/50 have been isolated, but the mutant gene(s) have not yet been identified. GP51 and GP44 each include a segment similar to a known RNA polymerase-binding motif, suggesting that GP51 may also act on RNA polymerase, although the RNA polymerase (RNAP) mutation that protects against GP44 does not protect against GP51/50. The effects on DNA and protein synthesis are probably indirect effects of the inhibition of host RNA synthesis.

We show that the products of SPO1 genes 44, 50, and 51 are required for the normal transition from early to middle gene expression during infection of *Bacillus subtilis* by bacteriophage SPO1; that they are also required for control of the shutoff of host DNA, RNA, and protein synthesis; and that their effects on host-shutoff could be accounted for by their effects on the regulation of gene expression. These three gene products had four distinguishable effects in regulating SPO1 gene expression: (1) GP44/50/51 acted to restrain expression of all SPO1 genes tested; (2) GP44 and/or GP50/51 caused additional specific repression of immediate-early genes; (3) GP44 and/or GP50/51 stimulated expression of middle genes; and (4) GP44 and/or GP50/51 stimulated expression of some delayed-early genes. Shutoff of immediate-early gene expression also required the activity of GP28, the middle gene-specific sigma factor. Shutoff of host RNA and protein synthesis was accelerated by either the 44- single mutant or the 50-51-double mutant, and more so by the 44-50-51-triple mutant. Shutoff of host DNA synthesis was accelerated by the mutants early in infection, but delayed by the 44-50-51 -triple mutant at later times. Although GP50 is a very small protein, consisting almost entirely of an apparent membrane-spanning domain, it contributed significantly to each activity tested. The combination clone of genes 44/50/51 is the most efficiently lethal constrict tested thus far (0.06% survival after 5 minutes induction).

Genes 45 and 46: Expression of genes 45/46 is lethal to *B. subtilis* and highly toxic to *E. coli*. DNA, RNA, and protein synthesis are all affected about equally, showing a decrease of about 50% in the first hour, and no further decrease in the next 2 hours. No information is available yet on the cellular target, but resistant mutants should be readily obtainable.

Individually, gene 46 is lethal but with diminished efficiency, and gene 45 is toxic but not lethal. Early results suggest that, during infection, a double mutant knocking out both genes is deficient in shutoff of host RNA and protein synthesis, but has no effect on host DNA synthesis.

Gene 47: Gene 47 has little or no effect when expressed in either *B. subtilis* or *E. coli*.

Genes 48 and 49: Gene 48 is strongly toxic but not lethal when expressed in either species. Although anomalies exist, the combination of genes 48 and 49 appears to be less toxic than 48 alone.

Genes 55–52: Expression of gene 52 is lethal to *E. coli*. Wild-type gene 52 has not yet been tested on *B. subtilis*. Expression of a clone with genes 55/54/53 is toxic, but not lethal. In a single experiment, the latter inhibited bacterial protein synthesis without affecting RNA synthesis. Expression of the full operon is toxic, but not consistently lethal. This is apparently accounted for by a transcription terminator located between genes 53 and 52. Mutants resistant to GCP52 have been isolated. The mutant gene(s) have not yet been identified, but while looking for them, several wild-type DNA segments whose over-expression protects against GP52 have been isolated. One of them includes a cluster of genes whose products are involved with protein synthesis, adding another suggestion that the gene 55 to 52 operon may target host protein synthesis. Gene 52 and gene 53 mutants are presently being isolated.

Genes 58–56: Expression of the whole operon is lethal to both species. Expression of 56 alone is lethal to *B. subtilis*, specifically inhibiting cell division, without affecting DNA synthesis or chromosomal segregation. Infection by SPO1 inhibits cell division, and a gene 56 mutation prevents that inhibition. *B. subtilis* mutants resistant to GP56 have been isolated, but the mutant gene(s) has not yet been identified.

Genes 60–59: The effects of GP59 and GP60 are uncertain because of apparent instability of the clone and inconsistency of data, but it appears that their expression may be lethal to *B. subtilis* in liquid culture but not on plates, while expression in *E. coli* is toxic, but not lethal.

Since some of these genes can kill both gram-positive (*B. subtilis*) and gram-negative (*E. coli*) bacteria, they would probably be lethal to most bacterial pathogens. The first three of the lethal mechanisms studied targeted at least three different bacterial processes (RNA synthesis for gene 44, cell division for gene 56, and both DNA synthesis and RNA synthesis for genes 38, 39, and 40). The lethal mechanisms studied target a panoply of bacterial processes and are thus ideally suited for the development of antimicrobial agents.

EXAMPLE 2

Mutational Analysis of Protein Role

We have performed mutational analysis in order to determine what the roles of the 24 genes and their proteins are in the host takeover by SPO1.

Regulatory roles of genes 44, 50, and 51: By site-specific mutagenesis, we have introduced a nonsense codon near the beginning of each of these genes, and have constructed all possible combinations of mutant genes. The nonsense mutations accelerated the rate of host-shutoff. FIG. 1 shows that shutoff of host RNA synthesis was accelerated by either the 44-single mutant or the 50-51-double mutant, and more so by the 44-50-51-triple mutant. Each data point in such an experiment represents the sum of host and phage RNA synthesis, so the decrease in total RNA synthesis by 12 minutes after infection provides a minimum estimate of the extent to which host RNA synthesis had been shut off. For wild-type and 44-50-51- these values were about 50% and 95%, respectively. The subsequent increases are due to increased phage RNA synthesis. Single mutants 50- and 51- had no significant effect (data not shown), showing that both GP50 and GP51 contribute to the activity of GP50/51.

Each of the three mutations contributed to this effect. 44- and 50-51 - each shut off host RNA synthesis more completely than wild-type, but less completely than the triple mutant. FIG. 7 shows that, while each of the 50- and 51-mutations had little effect by itself, each was necessary for the full effect of the triple mutant, 44-50-51-, and the double mutant, 50-51- (FIGS. 7a and 7b)

Similar results were seen when shutoff of host protein synthesis was measured by pulse-labeling with [$^3$H]leucine, or by SDS-polyacrylamide gel electrophoresis of proteins pulse-labeled with [$^{35}$S]-labeled amino acids. Thus, GP44/50/51 restrained the normal shutoff of host gene expression, and each of genes 44, 50, and 51 contributed significantly to that activity.

FIG. 2 shows that shutoff of host DNA synthesis was accelerated by the mutants early in infection, but delayed by the 44-50-51-triple mutant at later times. Only host DNA synthesis is assayed in such an experiment, since SPO1 incorporates hmUra into its DNA in place of thymine.

Thus, GP44/50/51 delayed the shutoff of host RNA synthesis, and both GP44 and GP50/51 contributed significantly to that activity. GP44/50/51 delayed the early component of the shutoff of host DNA synthesis, while a later component required the activity of GP44 and/or GP50/51.

Figure 12:
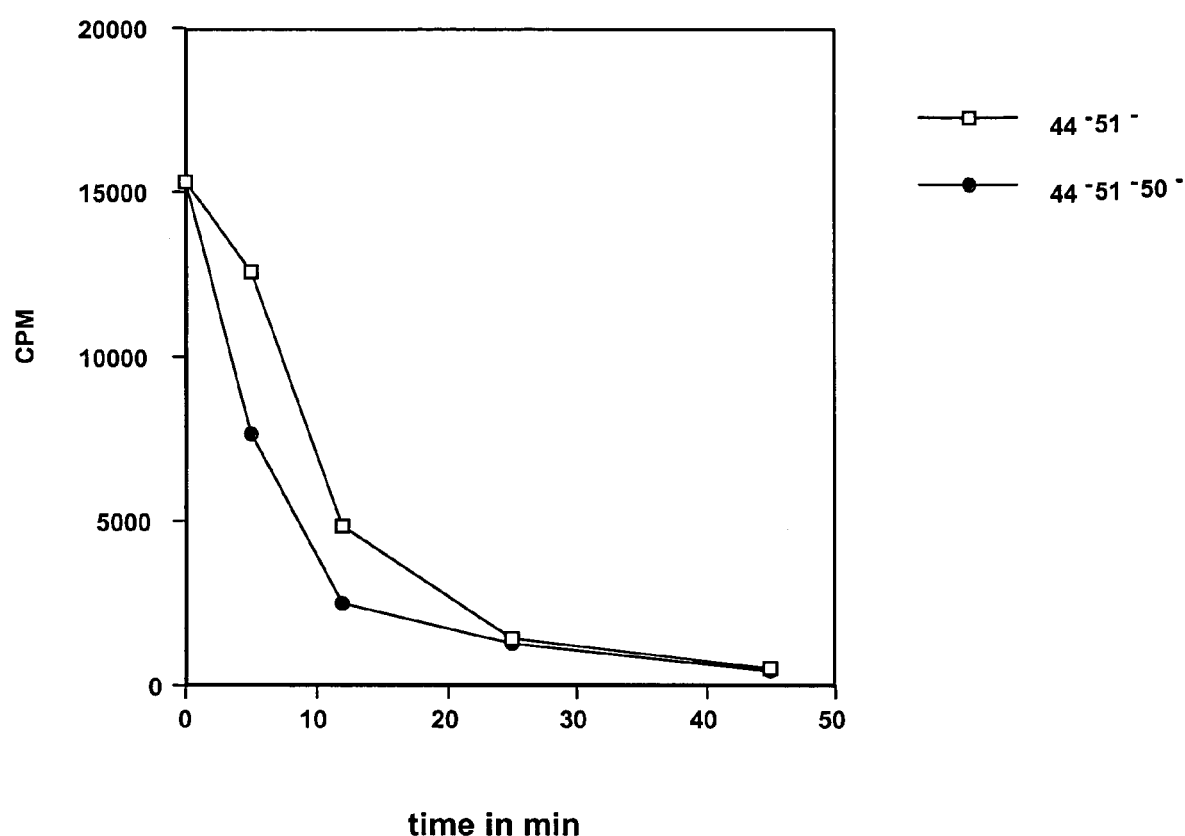
FIG. 12. Effect of GP50 on Host DNA Synthesis.

Independent Role of GP50: GP50 includes only 23 amino acids, and consists almost entirely of an apparent membrane-spanning domain, with charged amino acids at each end. It is important to demonstrate that such an unusual protein actually plays a functional role. The first 8 nucleotides of gene 50 overlap the last 8 nucleotides of gene 51, and the mutation that inactivates gene 50 also destroys the termination codon of gene 51, permitting GP51 to run on for about 30 more amino acids, beyond its normal 131. Thus, demonstration of an independent role for GP50 depends on the effects of adding the gene 50 mutation to strains that already have gene 51 inactivated. This is shown in FIG. 7 and FIG. 12.

Regulation of SPO1 gene expression. The negative effects of GP44/50/51 on shutoff of host RNA synthesis, and on the early phase of shutoff of host DNA synthesis, suggest that GP44/50/51 plays a regulatory role, rather than a directly causative role, in host-shutoff. We believe that we have identified the nature of that regulatory role, in that GP44/50/51 regulate the expression of all of the SPO1 genes known or expected to be involved in host-shutoff as shown in FIGS. 5 and 6. FIG. 5 shows that the triple mutant decreased transcription of at least some middle genes, while dramatically increasing transcription of all immediate-early genes. Thus the most obvious effect of GP44/50/51 is to facilitate the transition from immediate-early to middle gene expression.

However, when the data from 44- and 50-51- are considered, it's clear that these three gene products cause at least 4 distinguishable effects, which may be seen in FIG. 6. The immediate-early genes shown are representative of all known immediate-early genes. All of the known delayed early genes are shown, and the middle genes shown were the only ones assayed. Gene 27 is expressed from both an early and a middle promoter.

The first effect is the repression of all early and middle genes, which requires the activity of both GP44 and GP50/51. In comparison with wild-type, either the 44-mutation or the 50-51-double mutant caused increased expression of all genes tested, including immediate-early, delayed-early, and middle genes. Therefore, GP44/50/51 caused repression of all of the SPO1 genes tested, and the full effect of this repression required the activity of both GP44 and GP50/51.

The second effect is residual repression of immediate-early genes by either GP44 or GP50/51, even in the absence of the other. In comparison with 44- or 50-51-, the triple mutant 44-50-51-caused a further increase in expression of immediate-early genes. Therefore, there must be residual repressive activity present in the 44- or 50-51-strains, which is no longer there in 44-50-51-, and which therefore must be caused by GP50/51 in the 44-strain and by GP44 in the 50-51-strain.

The third effect is stimulation of expression of middle genes by either GP44 or GP50/51. In comparison with 44- or 50-51-, the triple mutant caused a decrease in expression of middle genes. Therefore, there must be an activity present in the 44- or 50-51-strains, which stimulates middle gene expression. Since that activity is no longer there in 44-50-51-, it must be caused by GP50/51 in the 44-strain and by GP44 in the 50-51-strain.

The fourth effect is stimulation of expression of certain delayed-early genes by either GP44 or GP50/51. In comparison with 44- or 50-51-, the triple mutant caused a decrease in expression of delayed-early genes 27 and 28. Therefore, there must be an activity present in the 44- or 50-51-strains, which stimulates delayed-early gene expression. Since that activity is no longer there in 44-50-51-, it must be caused by GP50/51 in the 44- strain and by GP44 in the 50-51-strain. With respect to delayed-early genes 37-40, such an activity can be seen for GP44 in the 50-51-strain, but not conclusively for GP50/51 in the 44-strain.

These effects of GP44/50/51 on regulation of expression of early and middle genes provide a plausible explanation for the effects of GP44/50/51 on host shutoff. The effect on shutoff of host RNA synthesis can be explained if one or more of the immediate-early genes, regulated by GP44/50/51, specifies a product that causes shutoff of host RNA synthesis. The over expression of such genes, caused by the triple mutant, could cause the accelerated shutoff of host RNA synthesis that was observed in triple mutant infection. The intermediate levels of over expression, caused by mutants 44- and 50-51-, could account for their also causing intermediate levels of accelerated shutoff of host RNA synthesis. Similarly, the deficient shutoff of host DNA synthesis by the triple mutant at middle times could be explained if that shutoff required one or more of the middle gene products whose expression is deficient in the triple mutant.

Alternative explanations, in which GP44/50/51 have activities, in addition to their regulation of SPO1 gene expression, which directly affect host shutoff, remain possible, although intuitively less likely because of their additional complexity. A possible explanation of the second and third effects is that GP44 or GP50/51 facilitates the displacement of $\sigma^4$ by GP28, but that is complicated by the fact that transcription of most host genes also requires $\sigma^4$. Under some conditions, rRNA synthesis is not shut off effectively by SPO1. Thus, a possible role of GP44/50/51 might be to prevent shutoff of rRNA synthesis, thereby accounting for some of the effect of 44-50-51- on RNA shutoff. All of these are potential subjects of future investigations.

The simplest hypothesis as to how GP44/50/51 regulate gene expression is that they interact with the host's RNAP to change its transcriptional specificity. Our earlier results had already suggested that RNAP was the cellular target for these proteins. When gene 44 was expressed in uninfected cells of either *B. subtilis* or *E. coli*, it caused the shutoff of bacterial RNA synthesis and cell death (Wei and Stewart, 1993, 1995). DNA and protein synthesis were also shut off, presumably as indirect results of the effect on RNA synthesis. An *E. coli* mutation substituting valine for glutamate at position 1272 of the beta subunit of the RNAP provided resistance to the lethal effects of gene 44 (Sampath, unpublished results). When the gene 50/51 operon was expressed in uninfected cells, it also caused the shutoff of RNA, DNA, and protein synthesis and cell death (our unpublished results). The products of both genes 44 and 51 include acidic/hydrophobic domains similar to the domain in *E. Coli* $\sigma^{54}$ that is required for binding to RNAP, and one segment of GP51 shows substantial similarity to the product of SPO1 gene 27, which is required for normal transcription of late genes (Greene et al., 1982; Stewart, 1993). Because of the very small size of GP50 (23 amino acids), its presence in the same operon with, and overlapping gene 51, and the synergistic effects of mutations in genes 50 and 51 we hypothesize that GP50 participates in the same activities as GP51. We suppose that the observed effects of GP44 or GP50/51 in uninfected cells are incidental consequences of their binding to RNAP, which causes effects in the opposite direction when in the context of phage infection.

Causative roles of genes 37, 38, 39, and 40 in host-shutoff. Nonsense mutations were introduced into each of genes 37 to 40 as described above. FIG. 3 shows that both the 40- and the 39-mutants are deficient in shutoff of host RNA synthesis, that 40- has the greater effect, and that the effects of the two mutations are not additive. These mutants had similar effects on shutoff of host protein synthesis (data not shown). However, as shown in FIG. 4, 40-inhibited but 39-accelerated the shutoff of host DNA synthesis, and 40-suppressed this effect of 39-. Apparently GP39 restrains the effect of GP40 on shutoff of host DNA synthesis, while both work in the same direction on host RNA synthesis. Both shutoffs occur so rapidly that it's unlikely that either effect of the 40-mutation is an indirect effect of the other. Genes 37–40 comprise one operon, with 38 and 39 overlapping slightly, suggesting the possibility of translational coupling and joint activity (Stewart et al., 1998). Preliminary results are consistent with GP37 and GP38 also participating in the same shutoffs. Thus, GP40 is required for normal shutoff of host DNA and RNA synthesis, and each of the other genes in this operon does or may play a significant role in each of those shutoffs.

Onset of Phage DNA Synthesis: FIG. 9 shows the effect of various of the mutant combinations on the onset of phage DNA synthesis. Each mutant combination that caused substantial delay in shutoff of host DNA synthesis also caused delay in phage DNA synthesis. This is probably because the continued use of cellular resources for host DNA synthesis meant that they were not fully available for phage DNA synthesis. Also contributing in most cases would be the diminished activity of phage genes required for phage DNA replication.

Single Step Growth Curves: FIGS. 10 and 11 show the effects of the various mutations on single step growth curves. Despite the profound effect of several of the multiple mutants on phage gene expression and DNA replication, production of progeny phage was only moderately affected. Each mutant that caused significant delay in phage DNA synthesis also caused a significant extension of the latent period. Only those mutants with a deficiency in phage DNA synthesis caused decreases in burst size. These were less than proportional to the decreases in DNA synthesis, suggesting that phage DNA is produced in excess in wild-type infections under these conditions.

EXAMPLE 3

Continued Analysis

For those genes whose lethality is not yet certain, we will determine the effects of gene expression unequivocally by cloning in more tightly controlled expression vectors. For each of these lethal genes and gene combinations, we will attempt to determine the mechanism by which it exerts its lethal effect.

To determine the cellular targets of the lethal proteins, we will select bacterial mutants resistant to each of the lethal genes, by plating, under inducing conditions, the strain carrying the lethal gene, and identifying those colonies whose resistance is caused by a chromosomal mutation. Each mutant gene will be identified, by screening a library of the chromosomal DNA for capacity to protect against the lethal effect of the phage gene. The methodology used will be similar to that described in Wei and Stewart (1995). Mutants resistant to 4 of the lethal genes have already been isolated, and in this manner the gene 44-resistant mutation was determined to be in the rpoB gene, specifying the B subunit of the RNA polymerase.

In case the protective mutation cannot be located by such a library screen (for instance because the protective mutation proves to be recessive, or because the protective gene proves to be unclonable), we will locate the protective mutation by genetic mapping. For *E. coli*, we will determine the approximate location by co-transfer with the Tn10 markers of the set of Hfr strains developed by Wanner (1986) and available from the *E. coli* Genetic Stock Center, and then determine the location more precisely by degree of linkage in P1 transduction (procedures as in Miller, 1992). For *B. subtilis*, we will determine the approximate location by showing linkage in PBS1 transduction with markers represented in the Dedonder et al. (1977) or Zahler (Vandeyar and Zahler, 1986) mapping kits, available from the *Bacillus* Genetic Stock Center. For finer structure mapping, we will look for the degree of co-transformation with markers within the region that showed high frequency co-transduction. The procedures are modifications of those described in Harwood and Cutting (1990). The availability of a complete set of mutants inactivating each gene in the *B. subtilis* genome (Kobayashi et al, 2003) will permit precise location of each affected gene, which will then be confirmed by nucleotide sequencing.

Identification of protein:protein interactions: To confirm the interaction of the lethal proteins with the targets thus tentatively identified, and to identify targets not found by such mutational analysis, host proteins that interact with each lethal SPO1 protein will be identified. We will make use of several genetic and physical techniques for identifying protein-protein interactions. Since such techniques can produce both false positives and false negatives (Legrain, 2002), we will use two or more of these techniques with each of the proteins. These techniques include:

Identification of cellular targets by genetic selection: Since these SPO1 proteins interfere with essential host processes, many of them are lethal when expressed individually in uninfected bacteria. Thus, their cellular targets may be identified by selecting bacterial mutants resistant to their lethal effects. Most of the proteins have similar effects on E. coli and B. subtilis (which share substantial homology), permitting the use of the more versatile E. coli cloning systems for initial identification of certain cellular targets. Targets initially identified in E. coli will be confirmed by testing the effect of the B. subtilis homolog.

E. coli mutants resistant to the lethal effect of GP44 were selected by plating under inducing conditions. One mutated gene identified was the rpoB gene (which specifies the beta subunit of RNAP), by screening a genomic library for capacity to protect against the lethal effect (Wei and Stewart, 1995; Sampath, unpublished results). Although alternative explanations are possible, this strongly suggests that GP44 targets the host RNAP. Similar analyses are in progress with others of the SPO1 lethal genes.

Pull-down assays. Proteins to be tested will either be expressed as glutathione-S-transferase (GST) fusions for attachment to glutathione sepharose beads (Pharmacia) or directly attached to N-hydroxysuccinimide (NHS)-activated sepharose resin (Pharmacia). The coupling of the NHS to primary amine is done under non-denaturing conditions at room temperature, and is quite efficient. Extracts of either infected or uninfected B. subtilis or E. coli cultures will be passed over the column, and the retained proteins will be eluted using increasing salt concentrations or urea denaturation. The eluant will then be subjected to SDS-PAGE, and the proteins electroeluted onto PVDF membranes for N-terminal sequencing and identification (Einarson and Orlinick, 2002).

Phage Display. Because only a few amino acids from one protein are needed to provide effective binding to another protein (Scott, 2001), it is not necessary to probe a library of whole proteins to identify binding partners. A phage display library (Willats, 2002; Barbas et al., 2001) displaying random sequence peptides 5 to 7 amino acids long will include most of the sequences necessary to confer specificity of binding to any protein. When a single protein is used to probe such a library, it can potentially identify the binding sequences of most or all proteins capable of binding to the probe protein. For instance, Malys et al. (2002) probed a random sequence peptide library with the T4 terminase protein, and identified all proteins previously known to bind to that protein, plus five other proteins whose binding was not previously known, but was subsequently confirmed in the one case conclusively tested.

Each of the proteins will be used to probe a random sequence peptide library, displayed on either phage T4 or phage M13. Several M13 libraries are available from New England Biolabs and have been used successfully in a long list of experiments (NEB, 2003). The peptide sequences identified as binding to each of the probe proteins will be used to probe the database of all B. subtilis and SPO1 gene products, thus identifying those proteins having segments capable of binding to the probe protein. The B. subtilis and E. coli genomes are completely known, and the virtually complete SPO1 sequence is also available (Hendrix et al., 2003).

Immunoprecipitation. Antibodies will be prepared against each of the proteins. Each antibody will be used to precipitate the targeted protein from extracts of infected cells, following procedures as described (Wei and Stewart, 1993; Wei and Stewart, 1995). The proteins in the precipitate will be identified using the same procedure as described.

Two-hybrid analysis. We anticipate that the above procedures will be sufficient to identify all or most of the proteins that interact with any of the lethal SPO1 proteins. However, if further information is needed, we will make use of a two-hybrid system. Noirot-Gros et al. (2002) described the use of yeast two-hybrid screens to identify many interactions between B. subtilis proteins, and this procedure can readily be adapted to interactions between SPO1 proteins and bacterial proteins.

EXAMPLE 4

Nonlytic Phage Therapy

Certain pathogens (e.g. E. coli O157:H7 or Neisseria meningitidis) cannot be treated with lytic phage or conventional antibiotics, because rapid destruction of the bacteria causes the precipitate release of lethal toxins that can kill the patient. The antimicrobial genes and peptides described herein solve this problem because each of them kills without lysing the bacterial cell. This has been documented directly for several of the genes by showing either microscopically or turbidimetrically that the structure of the cells remains intact even after they have lost viability. Maintenance of structural integrity can also be inferred for almost all of them, since all but gene 52 are expressed early during infection and expression of all early genes is insufficient to cause lysis during infection. Thus, the proteins could be used to treat such infections directly, or a temperate bacteriophage could be used to target the genes to the bacteria.

A transducing bacteriophage, specific for the particular pathogen, would introduce the lethal SPO1 gene(s), either on a plasmid that replicates in that bacterium or as part of a structure that would integrate into the bacterial genome. Exponential Biotherapies Inc. has successfully completed Phase 1 clinical trials of one of their first-generation phage therapy vehicles, a lytic phage that destroys pathogenic Enterococcus bacteria. They have patents on a method that selects for phages that survive in the circulation long enough to rescue animals from otherwise-lethal bacteremias (US20010026795 and US20010043924). The antimicrobial SPO1 genes would be used in the second generation of phage therapy vehicles, in which individual lethal genes or gene combinations would be delivered to the infecting bacteria by a transducing phage.

EXAMPLE 5

Peptidomimetics

To be effective therapeutically, the antibiotic activities characteristic of these various lethal proteins must be delivered to the infecting bacterial pathogen. This could be accomplished in any of several ways, one of which is to design small molecule drugs that mimic the active sites of the proteins. To be effective, the antibiotic characteristic of various lethal proteins must be delivered to the infecting bacterial pathogen, in concentrations high enough to be therapeutic. By designing small molecule drugs that mimic the active sites of the lethal proteins, but that have favorable pharmacological characteristics with regard to delivery, uptake, human toxicity, and potency, a directed peptidomimetic molecule can be designed. Examples of successful use of such peptidomimetic small molecules include: Tian et al., 1998; Salvemini et al., 1999, 2002; Andrade-Gordon et al., , 1999; Wrighton and Gearing, 1999; Zhang, 2000; Ohkanda et al., 2001; Smith et al., 2001; Air et al., 2002; Gadek et al., 2002; Fotsch et al., 2003; and Martin et al., 2003.

Structures of the lethal proteins will be determined. The lethal SPO1 proteins are relatively small (ranging from 77 to 255 amino acids) so we can determine their structures by X-ray crystallography and/or NMR spectroscopy. Each functional site will be identified by 1) mutagenesis of the cloned gene, 2) selection for mutants that have lost their lethal activity, and 3) identification of the positions of the mutant amino acids in the 3-dimensional structures. Similarly, the structures of the target molecules will be determined, and the targeted surfaces identified by the positions of mutations causing resistance to the lethal proteins. Where possible, we will co-crystallize the lethal protein with the target molecule, to determine changes in structure caused by their interaction.

Small molecules can then be designed that attempt to mimic the structure of the active site. High throughput screening of many candidate molecules for binding to the target protein or inhibition of its function, depending on the specific target identified, will provide lead molecules for peptidomimetic chemicals.

Preparation for X-ray crystallography. The lethal SPO1 proteins are relatively small (ranging from 77 to 255 amino acids) and their origins in a prokaryotic host make it likely that the proteins will be correctly folded on expression. Each of the purified proteins will be tested by light scattering and native gel electrophoresis to determine whether the samples are monodisperse. Most proteins will be tested for proper folding, by taking their Heteronuclear-Single Quantum Correlation (HSQC) spectra, using either the 500 or 600 MHz NMR at Rice University. To do this, the proteins will be $^{15}$N-labeled by growing cells in minimal media supplemented with $^{15}$N-ammonium chloride. Proteins that are partially unfolded can be rapidly identified by $^{15}$N-HSQC NMR spectra, and the salt, pH and ligand conditions can be adjusted to provide a homogeneous, well-folded sample suitable for X-ray diffraction studies. Proteins that are well-folded and active will then be subjected to a sparse-matrix crystallization protocol to identify conditions appropriate for macromolecular crystal growth. The smaller proteins such as GP46 and GP56 would also be amenable to structure determination by NMR. They will be isotopically labeled with $^{15}$N or $^{15}$N and $^{13}$C and their structures determined by multidimensional heteronuclear NMR methods. In cases where a toxic protein is expressed in limited quantities, we will skip the NMR screening and proceed directly to crystallography.

High-throughput crystallographic screening. The Rice University Crystallography Core Facility uses a MATRIX TECHNOLOGIES® HYDRA II-PLUS ONE™ liquid-handling robot and automated imaging microscope, for high-throughput crystallographic screening (Diversified Scientific). Such facilities give us the ability to rapidly screen far more crystallographic conditions with far less material than traditional vapor diffusion methods. This is particularly useful for proteins whose yield has been limited due to their toxic nature. Using our high-throughput facilities, 1 mg of protein at 10 mg/ml can be subjected to 500 trial conditions, as compared to 100 using manual methods. Analysis is facilitated by construction of relational databases for correlation of high-throughput crystallization data with incomplete-factorial sparse matrix generation and development of new second generation matrices derived from the observed trials. Recent studies from the NIH structural genomics initiative have suggested that in 90% of cases of a monodisperse and well-folded protein where a crystallization condition is found, the condition was found in only ~200–500 trials. Failure to obtain crystals with good diffraction properties after 500 trials suggests that either addition of a ligand/cofactor or partial proteolysis studies may be appropriate for further trials. Once crystallization conditions have been identified, structures will be determined using either Multiwavelength Anomalous Diffraction (MAD) (Hedrickson and Ogata, 1997) or Multiple Isomorphous Replacement (MIR) (McPherson, 1999). Model building and refinement (Shamoo et al., 1995, Shamoo and Steitz, 1999) provides additional information from small sample sizes and allows generation of ideal peptidomimetic structures.

Mutagenesis. To map the functional site of each of the lethal proteins, genes encoding the lethal proteins will be subjected to error prone PCR in vitro (Spee et al., 1993; Miyazaki et al., 2000) and then reintroduced back into either E. coli or B. subtilis by transformation. Mutations that strongly reduce or abolish host lethality will be selected by survival of the host to form colonies. Sequencing of the mutants will permit mapping the changes onto the protein's primary structure, and thus onto the three-dimensional structure as determined above, hopefully providing a tentative identification of the active site.

Structure of target molecules and target sites. It should be possible to identify the target site within the target molecule, by identifying the amino acids whose mutation protects the target against the activity of the lethal protein, and finding which of those amino acids in the wild-type protein form a surface complementary to the binding surface of the lethal protein. Thus, when a target has been identified, the wild-type gene specifying it will be cloned and subjected to mutagenesis by error prone PCR. The library consisting of that mutagenized population will be transformed back into the host cells, selecting for mutants resistant to the lethal protein. The position of the mutations will be determined by nucleotide sequencing, and those positions mapped onto the 3-dimensional structure. In cases where the target structure is not known, we will determine it whenever possible. Such analysis will allow us to determine a possible mechanism of action; for example resistant mutations may map to a known protein-protein contact surface or active site. We can then develop an accurate structure-function characterization of the host-SPO1 protein interaction and mechanism.

To minimize the likelihood of toxic side effects when the peptidomimetic molecules are introduced into clinical use, our highest priorities for the above analyses will be those of the lethal SPO1 proteins that do not target a protein with an obvious human homolog. However, even those whose target does have a human homolog might be worth pursuing, since the target may function differently or be less accessible in human cells.

EXAMPLE 6

Antimicrobial Treatments

Information already in hand about some of these lethal proteins shows that they target a variety of different bacterial processes, so we expect to develop a panoply of different antibiotic mechanisms, each targeting a different bacterial process. Since none of the lethal gene products show substantial homology to any known protein, it is highly probable that each mechanism will be novel, meaning that bacteria resistant to currently used antibiotics should be susceptible to each of the antibiotics based on these lethal proteins.

The antibiotics to be developed would have the following advantages: (1) targeting of a wide spectrum of gram-positive and gram-negative bacterial pathogens; (2) effectiveness against anthrax, plague, and other anticipated agents of biological warfare; (3) effectiveness against bacteria that are resistant to presently known antibiotics; (4) inclusion of a diverse spectrum of antibiotic mechanisms; and (5) minimal release of lethal toxins during treatment.

Combining two or more lethal genes in the same clone can form more efficiently lethal constructs. For instance, the triplet combination of genes 44, 50, and 51 kills more than 20 times as efficiently as either of its components cloned individually in the same vector (0.06% survival after 5 minutes induction).

Since few, if any, existing antibiotics are based on a specific bacteriophage gene, and since few, if any, of the lethal SPO1 gene products show substantial homology to any protein presently in the public database, it is likely that each lethal mechanism will be novel. This should help avoid the resistance mechanisms of the current generation of resistant bacteria.

All of the references cited herein are expressly incorporated by reference. References are listed again here for convenience:

1. US20010026795, Canton, et at. Exponential Biotherapies, Inc. Pub. Nov. 22, 2001.
2. US20010043924, Merril, et at. Exponential Biotherapies, Inc. Pub. Oct. 4, 2001.
3. Air, E. L., et al. (2002) Nature Med. 8: 179–183.
4. Andrade-Gordon, P. et at. (1999) Proc. Natl. Acad. Sci. U.S. 96: 12257–12262.
5. Barbas, C. F., III, et al. (2001) Cold Spring Harbor Laboratory Press, Cold Spring Harbor, New York.
6. Dedonder, R. A., et al. (1977) Appl. Environ. Mirobiol. 33: 989–993.
7. Einarson, M. B., and J. R. Orlinick. (2002) in Golemis, E. (ed.), Cold Spring Harbor Laboratory Press, Cold Spring Harbor, New York. pp. 37–58
8. Fotsch, C., et al. (2003) Bioorganic & Medicinal Chemistry Letters 13: 2337–40.
9. Gadek, T. R., et al. (2002) Science 295: 1086–9.
10. Greene, J. R., et al. (1982) J. Virol. 41: 715–20.
11. Greene, J. R. et at. (1984) Proc. Natl. Acad. Sci. USA 81: 7031–5.
12. Harwood, C. R., and S. M. Cutting (eds.) (1990) John Wiley & Sons. New York.
13. Hedrickson, W. A., and C. M. Ogata. (1997) Meth. Enz. 276: 494–522.
14. Hendrix, R., et al. (2003) http://pbi.bio.pitt.edu/
15. Ireton, K., et al. (1993) Genes & Dev. 7: 283–94.
16. Kim, L., et al. (1996) Gene 181: 71–6.

-continued

17. Kobayashi, K., et al. (2003) Proc. Natl. Acad. Sci. USA 100: 4678–83.
18. Legrain, P. (2002) Nature Biotechnology 20: 128–9.
19. Malys, N., et al. (2002) J. Mol. Biol. 319: 289–04.
20. Martin, .L., et al. (2003) Nature Biotech. 21: 71–6.
21. McPherson, A. (1999) Crystallization of Biological Macromolecules. Cold Spring Harbor Laboratory Press.
22. Miller, J. H. (1992) Cold Spring Harbor Laboratory Press, Cold Spring Harbor, New York.
23. Miyazaki, K., et al. (2000) J. Mol. Biol. 297: 1015–26.
24. New England Biologicals (2003) http://wwxv.neb.com/neb/products/drug_discovery/phdrefs.html.
25. Noirot-Gros, M.-F., et al. (2002) Proc. Natl. Acad. Sci. U.S.A. 99: 8342–8347.
26. Ohkanda, J., et al. (2001) Bioorganic & Medicinal Chemistry Letters 11: 761–764.
27. Okubo, S., et al. (1972) Biken J. 15: 81–97.
28. Salvemini, D., et al. (1999) Science 286: 304–6.
29. Salvemini, D., et al. (2002) Nature Reviews 1: 367–74.
30. Sampath, A., et al. (2001) In Abstracts of the Fourteenth Evergreen International Phage Biology Meeting, Poster Section. August 8–13.
31. Sampath, A., and C. R. Stewart (2003) Accepted for publication in J. Bacteriol. with revisions.
32. Sayers, J. R. (1996) Meth. Enz. 275: 227–38.
33. Scarlato, V., and S. Gargano (1992) Gene 118: 109–113.
34. Scott, J. K. (2001) in "Phage Display" C. F. Barbas, et al. (eds.) Cold Spring Harbor Laboratory Press, Cold Spring Harbor, New York. pp. 4.1–4.13.
35. Shamoo, Y., et al. (1993) Nat. Struc. Biol. 4: 215–222.
36. Shamoo, Y., et al. (1995) Nature 376: 362–6.
37. Shamoo, Y., et. al. (1997) Nat. Struc. Biol. 4: 215–22.
38. Sharnoo, Y., and T. A. Steitz. (1999) Cell 99: 155–166.
39. Spee, J. H., et al. (1993) Nucleic Acids Res. 21: 777–8.
40. Smith, R.A., et al. (2001) Bioorganic and Medical Chemistry Letters 11: 2951–4.
41. Stewart, C. R. (1993) in *Bacillus subtilis* and other gram-positive bacteria (A. Sonenshein, J. A. Hoch, and R. Losick, eds. American Society for Microbiology) pp. 813–29.
42. Stewart, C. R. (1997) GenBank Acc. No. AF031901.
43. Stewart, C. R., et al. (1998) Virology. 246: 329–40.
44. Stewart, C. R. (1999) SPO1 Phage (Myoviridae), in Encyclopedia of Virology (2nd Edition, Webster, R. G., and Granoff, A., eds.) pp. 1681–5.
45. Stewart, C. R. et al. (Aug. 8–13, 2001) In Abstracts of the Fourteenth Evergreen International Phage Biology Meeting.
46. Tatusova, T. A. & T. L. Madden (1999) FEMS Microbiol. Lett. 174: 247–50.
47. Tian, S. S., et al. (1998) Science 281: 257–59.
48. Vandeyar, M. A., and S. A. Zahler (1986) J. Bacteriol. 167: 530–4.
49. Wanner, B. L. (1986) J. Mol. Biol. 191: 39–58.
50. Wei, P., and C. R. Stewart. (1993) J. Bacteriol. 175: 7887–900.
51. Wei, P. and C. R. Stewart (1995) J. Bacteriol. 177: 2933–7.
52. Willats, W. G. T. (2002) Plant Molecular Biology 50: 837–54.
53. Wrighton, N., and D. Gearing (1999) Nature Biotech. 17: 1157–8.
54. Zhang, H-T., et al. (2002) Drug News Perspect. 13: 325–9.

We claim:

1. A method of inhibitiing bacterial infection in a mammal wherein said infection is caused by *Bacillus* or *Escheria* bacterium, said method comprising administering to said mammal a protein comprising a sequence selected from the group consisting of: i) SEQ ID No: 8; and ii) a sequence which has 95% identity to SEQ ID No: 8, in an amount effective to kill said bacteria.

2. The method of claim 1, wherein the protein is delivered by direct administration of the protein.

3. The method of claim 1, wherein the protein comprises a combination of proteins including SEQ ID NO: 8 and having sequences selected from the group consisting of SEQ ID NO: 1; SEQ ID NO: 2, SEQ ID NO: 3; SEQ ID NO: 4; SEQ ID NO: 5; SEQ ID NO: 7; SEQ ID NO: 9; SEQ ID NO: 10; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 2 and 3; SEQ ID NO: 3 and 4; SEQ ID NO: 2, 3, and 4; SEQ ID NO: 1, 2, 3, and 4; SEQ ID NO: 9 and 10; SEQ ID NO: 14 and 15; SEQ ID NO: 16, 17, and 18; SEQ ID NO: 17 and 18; SEQ ID NO: 16, 17, 18, and 19; SEQ ID NO: 17, 18, and 19; and SEQ ID NO: 20, 21, and 22.

4. The method of claim 3, wherein the proteins have the sequences of SEQ ID NO: 8, 14, and 15.

5. The method of claim 1, wherein the protein is fused to a cationic agent, a hydrophobic agent, a signal sequence, a lipid or combinations thereof, and is delivered by a method selected from: inhalation of an aerosolized anti-bacterial peptide; topical application; injection; and oral ingestion.

6. A method of inhibiting bacterial infection in a mammal wherein said infection is caused by *Bacillus* or *Escheria* bacterium, said method comprising administering to said mammal a pharmaceutical comprising a composition selected from the groups consisting of a bactericidal SPO1 protein comprising SEQ ID No: 8 and a combination of bactericidal SPO1 proteins including a protein comprising SEQ ID No: 8, in an amount effective to kill said bacteria.

7. The method of claim 6, wherein said combination of bactericidal SPO1 proteins comprises one or more sequences selected from the group consisting of: i) SEQ ID NO: 1–5, 7, 9, 10, and 12–24; and ii) a sequence which has 95% identity to a sequence in i).

8. A method of inhibiting bacterial infection in a mammal wherein said infection is caused by *Bacillus* or *Escheria* bacterium, said method comprising administering to said mammal a pharmaceutical comprising a combination of bactericidal SPO1 proteins, wherein said combination comprises a protein of SEQ ID No: 8 and one or more proteins selected from the groups consisting of SEQ ID No: 1–5, 7, 9, 10 and 12–24, in an amount effective to inhibit the growth of said bacteria.

9. The method of claim 8, wherein said combination comprises a protein selected from the group consisting of SEQ ID NO: 2 and 3; SEQ ID NO: 3 and 4; SEQ ID NO: 2, 3, and 4; SEQ ID NO: 1, 2, 3, and 4; SEQ ID NO: 9 and 10; SEQ ID NO: 14 and 15; SEQ ID NO: 16, 17, and 18; SEQ ID NO: 17 and 18; SEQ ID NO: 16, 17, 18, and 19; SEQ ID NO: 17, 18, and 19; and SEQ ID NO: 20, 21, and 22.

10. The method of claim 8, wherein said combination comprises a protein selected from the group consisting of SEQ ID NO: 14 and SEQ ID NO: 15.

11. The method of claim 8, wherein said combination comprises SEQ ID NO: 14and SEQ ID NO: 15.

* * * * *